United States Patent
Onken et al.

(10) Patent No.: US 10,350,366 B2
(45) Date of Patent: Jul. 16, 2019

(54) SAFE CANNULATION DEVICES, METHODS, AND SYSTEMS

(71) Applicant: NXSTAGE MEDICAL, INC., Lawrence, MA (US)

(72) Inventors: Matthew Onken, Acton, MA (US); Steven Belletti, Hooksett, NH (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 718 days.

(21) Appl. No.: 14/763,808

(22) PCT Filed: Jan. 31, 2014

(86) PCT No.: PCT/US2014/014256
§ 371 (c)(1),
(2) Date: Jul. 27, 2015

(87) PCT Pub. No.: WO2014/121119
PCT Pub. Date: Aug. 7, 2014

(65) Prior Publication Data
US 2015/0359973 A1    Dec. 17, 2015

Related U.S. Application Data

(60) Provisional application No. 61/759,666, filed on Feb. 1, 2013.

(51) Int. Cl.
*A61M 5/32* (2006.01)
*A61M 25/06* (2006.01)

(52) U.S. Cl.
CPC ............ *A61M 5/3202* (2013.01); *A61M 5/32* (2013.01); *A61M 25/0631* (2013.01); *A61M 25/0637* (2013.01)

(58) Field of Classification Search
CPC ..................... A61M 25/0631; A61M 25/0637
See application file for complete search history.

(56) References Cited

U.S. PATENT DOCUMENTS 3,782,383 A    1/1974   Thompson et al.
4,170,993 A   10/1979   Alvarez
(Continued)

FOREIGN PATENT DOCUMENTS

DE    19543313 A1    6/1997
EP     0425448 B1    1/1995
(Continued)

OTHER PUBLICATIONS

US 8,308,694 B1, 11/2012, Kuracina et al. (withdrawn)
(Continued)

*Primary Examiner* — Amber R Stiles
*Assistant Examiner* — Matthew A Engel
(74) *Attorney, Agent, or Firm* — Potomac Law Group, PLLC; Mark A. Catan

(57) ABSTRACT

Methods and devices for use and handling of intravenous and/or subcutaneous needles, and, more particularly, to safety devices for shielding needles or other sharp articles or devices that present a safety hazard are disclosed. In an embodiment, a needle protective sheath can include a top wall, a bottom wall, and a pair of side walls joining the top and bottom walls. A finger shield extends from the top wall at a front opening of the sheath and is attached to the top wall by a hinge portion. The finger shield can be rotated about the hinge portion to block the front opening so as to secure a needle within the sheath.

6 Claims, 14 Drawing Sheets

(56) References Cited

U.S. PATENT DOCUMENTS

| | | |
|---|---|---|
| 4,194,504 A * | 3/1980 | Harms .............. A61M 25/0014 604/165.03 |
| 4,625,898 A | 12/1986 | Hazard |
| 4,631,057 A | 12/1986 | Mitchell |
| 4,631,058 A | 12/1986 | Raines |
| 4,693,708 A | 9/1987 | Wanderer et al. |
| 4,874,383 A | 10/1989 | McNaughton |
| 4,906,235 A | 3/1990 | Roberts |
| 4,935,012 A | 6/1990 | Magre et al. |
| 4,941,881 A | 7/1990 | Masters et al. |
| 4,950,242 A | 8/1990 | Alvarez |
| 4,985,020 A | 1/1991 | Kasuya |
| 5,009,640 A | 4/1991 | Pyret et al. |
| 5,092,493 A | 3/1992 | Pehr |
| 5,112,311 A | 5/1992 | Utterberg et al. |
| 5,120,311 A | 6/1992 | Sagstetter et al. |
| 5,266,072 A | 11/1993 | Utterberg et al. |
| 5,401,250 A | 3/1995 | Shields |
| 5,433,703 A | 7/1995 | Utterberg et al. |
| 5,562,636 A | 10/1996 | Utterberg |
| 5,562,637 A | 10/1996 | Utterberg |
| 5,573,512 A | 11/1996 | van den Haak |
| 5,672,160 A | 9/1997 | Osterlind et al. |
| 5,683,365 A | 11/1997 | Brown et al. |
| 5,685,862 A | 11/1997 | Mahurkar |
| 5,704,917 A | 1/1998 | Utterberg |
| 5,704,919 A | 1/1998 | Kraus et al. |
| 5,704,924 A | 1/1998 | Utterberg et al. |
| 5,718,239 A | 2/1998 | Newby et al. |
| 5,743,882 A | 4/1998 | Luther |
| 5,746,215 A | 5/1998 | Manjarrez |
| 5,772,638 A | 6/1998 | Utterberg et al. |
| 5,807,351 A | 9/1998 | Kashmer |
| 5,827,239 A | 10/1998 | Dillon et al. |
| 5,833,670 A | 11/1998 | Dillon et al. |
| 5,836,917 A | 11/1998 | Thorne et al. |
| 5,882,337 A | 3/1999 | Bogert et al. |
| 5,891,099 A | 4/1999 | Nakajima et al. |
| 5,921,969 A | 7/1999 | Vallelunga et al. |
| 5,951,529 A | 9/1999 | Utterberg |
| 6,013,059 A | 1/2000 | Jacobs |
| 6,093,172 A | 7/2000 | Funderburk et al. |
| 6,106,499 A | 8/2000 | Overton et al. |
| 6,193,694 B1 | 2/2001 | Bell et al. |
| 6,228,049 B1 | 5/2001 | Schroeder et al. |
| 6,235,006 B1 | 5/2001 | Dillon et al. |
| 6,280,420 B1 | 8/2001 | Ferguson et al. |
| 6,298,541 B1 | 10/2001 | Newby et al. |
| 6,309,376 B1 | 10/2001 | Alesi |
| 6,322,551 B1 | 11/2001 | Brugger |
| 6,355,021 B1 | 3/2002 | Nielsen et al. |
| 6,398,743 B1 | 6/2002 | Halseth et al. |
| 6,436,086 B1 | 8/2002 | Newby et al. |
| 6,440,104 B1 | 8/2002 | Newby et al. |
| 6,517,522 B1 | 2/2003 | Bell et al. |
| 6,537,259 B1 | 3/2003 | Niermann |
| 6,554,807 B2 | 4/2003 | Gollobin |
| 6,592,556 B1 | 7/2003 | Thorne |
| 6,595,955 B2 | 7/2003 | Ferguson et al. |
| 6,595,965 B1 | 7/2003 | Utterberg |
| 6,623,461 B1 | 9/2003 | Wilkinson et al. |
| 6,629,959 B2 | 10/2003 | Kuracina et al. |
| 6,632,201 B1 | 10/2003 | Mathias et al. |
| 6,695,819 B2 | 2/2004 | Kobayashi |
| 6,699,217 B2 | 3/2004 | Bennett et al. |
| 6,719,737 B2 | 4/2004 | Kobayashi |
| 6,780,169 B2 | 8/2004 | Crawford |
| 6,796,962 B2 | 9/2004 | Ferguson et al. |
| 6,832,992 B2 | 12/2004 | Wilkinson |
| 6,835,190 B2 | 12/2004 | Nguyen |
| 6,869,418 B2 | 3/2005 | Marano-Ford |
| 6,902,546 B2 | 6/2005 | Ferguson |
| 6,918,891 B2 | 7/2005 | Bressler et al. |
| 6,926,700 B2 | 8/2005 | Bressler et al. |
| 6,932,803 B2 | 8/2005 | Newby |
| 6,936,036 B2 | 8/2005 | Wilkinson et al. |
| 6,984,223 B2 | 1/2006 | Newby et al. |
| 6,997,913 B2 | 2/2006 | Wilkinson |
| 7,004,927 B2 | 2/2006 | Ferguson et al. |
| RE39,107 E * | 5/2006 | Shaw ................ A61B 5/15003 600/576 |
| 7,037,292 B2 | 5/2006 | Carlyon et al. |
| 7,112,190 B2 | 9/2006 | Bressler et al. |
| 7,115,112 B2 | 10/2006 | Mogensen et al. |
| 7,128,726 B2 | 10/2006 | Crawford et al. |
| 7,147,623 B2 | 12/2006 | Mathiasen |
| 7,163,526 B2 | 1/2007 | Leong et al. |
| 7,175,610 B2 | 2/2007 | Mori |
| 7,179,244 B2 | 2/2007 | Smith et al. |
| 7,198,618 B2 | 4/2007 | Ferguson et al. |
| 7,220,249 B2 | 5/2007 | Hwang et al. |
| 7,258,680 B2 | 8/2007 | Mogensen et al. |
| D554,253 S | 10/2007 | Kornerup |
| 7,341,573 B2 | 3/2008 | Ferguson et al. |
| 7,377,911 B2 | 5/2008 | Kunitomi et al. |
| 7,407,493 B2 | 8/2008 | Cane' |
| 7,413,562 B2 | 8/2008 | Ferguson et al. |
| D576,267 S | 9/2008 | Mogensen et al. |
| 7,422,573 B2 | 9/2008 | Wilkinson et al. |
| D579,541 S | 10/2008 | Mogensen et al. |
| 7,458,954 B2 | 12/2008 | Ferguson et al. |
| 7,481,794 B2 | 1/2009 | Jensen |
| 7,566,327 B2 | 7/2009 | Mathias |
| 7,591,804 B2 | 9/2009 | Utterberg et al. |
| 7,594,909 B2 | 9/2009 | Mogensen et al. |
| 7,611,485 B2 | 11/2009 | Ferguson |
| 7,611,486 B2 | 11/2009 | Jones et al. |
| 7,618,395 B2 | 11/2009 | Ferguson |
| 7,621,395 B2 | 11/2009 | Mogensen et al. |
| 7,625,357 B2 | 12/2009 | Yang |
| 7,632,252 B2 | 12/2009 | Prais et al. |
| 7,648,480 B2 | 1/2010 | Bosel et al. |
| 7,648,494 B2 | 1/2010 | Kornerup et al. |
| 7,654,484 B2 | 2/2010 | Mogensen et al. |
| 7,654,735 B2 | 2/2010 | Sisk et al. |
| 7,717,888 B2 | 5/2010 | Vaillancourt et al. |
| 7,802,824 B2 | 9/2010 | Christensen et al. |
| 7,833,217 B2 | 11/2010 | Boulis |
| 7,867,200 B2 | 1/2011 | Mogensen |
| 7,972,309 B2 | 7/2011 | Crawford |
| 7,985,199 B2 | 7/2011 | Kornerup et al. |
| 8,002,746 B2 | 8/2011 | Erskine |
| 8,012,126 B2 | 9/2011 | Tipsmark et al. |
| 8,062,250 B2 | 11/2011 | Mogensen et al. |
| 8,066,678 B2 | 11/2011 | Vaillancourt et al. |
| 8,096,977 B2 | 1/2012 | Ayiyama et al. |
| D655,807 S | 3/2012 | Mogensen et al. |
| 8,152,771 B2 | 4/2012 | Mogensen et al. |
| 8,162,892 B2 | 4/2012 | Mogensen et al. |
| 8,172,805 B2 | 5/2012 | Mogensen et al. |
| 8,172,809 B2 | 5/2012 | Ferguson et al. |
| 8,221,352 B2 | 7/2012 | Merchant |
| 8,221,355 B2 | 7/2012 | Kornerup et al. |
| 8,231,582 B2 | 7/2012 | Vaillancourt et al. |
| 8,246,588 B2 | 8/2012 | Gyrn |
| 8,273,056 B2 | 9/2012 | Kuracina et al. |
| 8,277,408 B2 | 10/2012 | Crawford et al. |
| 8,287,498 B2 | 10/2012 | Tan et al. |
| 8,287,516 B2 | 10/2012 | Kornerup et al. |
| 8,303,549 B2 | 11/2012 | Mejlhede et al. |
| 8,430,850 B2 | 4/2013 | Gyrn et al. |
| D682,415 S | 5/2013 | Mogensen et al. |
| 8,439,838 B2 | 5/2013 | Mogensen et al. |
| 8,486,003 B2 | 7/2013 | Nielsen |
| 8,486,015 B2 | 7/2013 | Carlyon et al. |
| 8,535,273 B2 | 9/2013 | Vaillancourt et al. |
| 8,562,567 B2 | 10/2013 | Gundberg |
| 8,574,197 B2 | 11/2013 | Halseth et al. |
| 8,597,253 B2 | 12/2013 | Vaillancourt |
| 8,672,895 B2 | 3/2014 | Kuracina et al. |
| 8,696,594 B2 * | 4/2014 | Mahurkar .......... A61B 5/15003 600/564 |
| 8,708,977 B2 | 4/2014 | Bressler et al. |
| 8,728,029 B2 | 5/2014 | Vaillancourt et al. |

(56) References Cited

U.S. PATENT DOCUMENTS

| | | |
|---|---|---|
| 8,747,355 B2 | 6/2014 | Rubinstein et al. |
| 8,747,428 B2 | 6/2014 | Fischell et al. |
| 8,764,711 B2 | 7/2014 | Kuracina et al. |
| 8,790,311 B2 | 7/2014 | Gyrn |
| 8,821,439 B2 | 9/2014 | Kuracina et al. |
| 8,845,584 B2 | 9/2014 | Ferguson et al. |
| 8,852,154 B2 | 10/2014 | Halseth et al. |
| 8,939,938 B2 | 1/2015 | Funamura et al. |
| 8,945,057 B2 | 2/2015 | Gyrn et al. |
| 8,968,240 B2 | 3/2015 | Erskine |
| 9,028,447 B2 | 5/2015 | Baid |
| 9,095,651 B2 | 8/2015 | Ng et al. |
| 2002/0077611 A1 | 6/2002 | von Dyck et al. |
| 2003/0055381 A1 | 3/2003 | Wilkinson |
| 2003/0125676 A1 | 7/2003 | Swenson et al. |
| 2003/0181873 A1 | 9/2003 | Swenson |
| 2003/0208160 A1 | 11/2003 | Crawford |
| 2004/0049159 A1 | 3/2004 | Barrus et al. |
| 2004/0153039 A1 | 8/2004 | Wang |
| 2004/0171995 A1 | 9/2004 | Niermann |
| 2004/0176730 A1 | 9/2004 | Wang |
| 2005/0070849 A1 | 3/2005 | Yang |
| 2005/0090783 A1 | 4/2005 | Sibbitt |
| 2005/0240154 A1 | 10/2005 | Mogensen et al. |
| 2006/0100581 A1 | 5/2006 | Mogensen |
| 2007/0250014 A1* | 10/2007 | Utterberg .......... A61M 25/0631 604/192 |
| 2010/0082002 A1 | 4/2010 | Baid |
| 2012/0029421 A1 | 2/2012 | Drake et al. |
| 2014/0135713 A1 | 5/2014 | Domonkos |
| 2014/0148765 A1 | 5/2014 | Li |
| 2014/0221872 A1 | 8/2014 | Lin |

FOREIGN PATENT DOCUMENTS

| | | |
|---|---|---|
| EP | 0984808 B1 | 6/2004 |
| JP | 2001-259029 A | 9/2001 |
| JP | 4115587 B2 | 7/2008 |
| JP | 4137426 B2 | 8/2008 |
| JP | 4249999 B2 | 4/2009 |
| WO | WO 2002/026284 A2 | 4/2002 |
| WO | WO 2002/092160 A1 | 11/2002 |

OTHER PUBLICATIONS

International Search Report and Written Opinion for International Application No. PCT/US14/14256, dated Apr. 22, 2014.

* cited by examiner

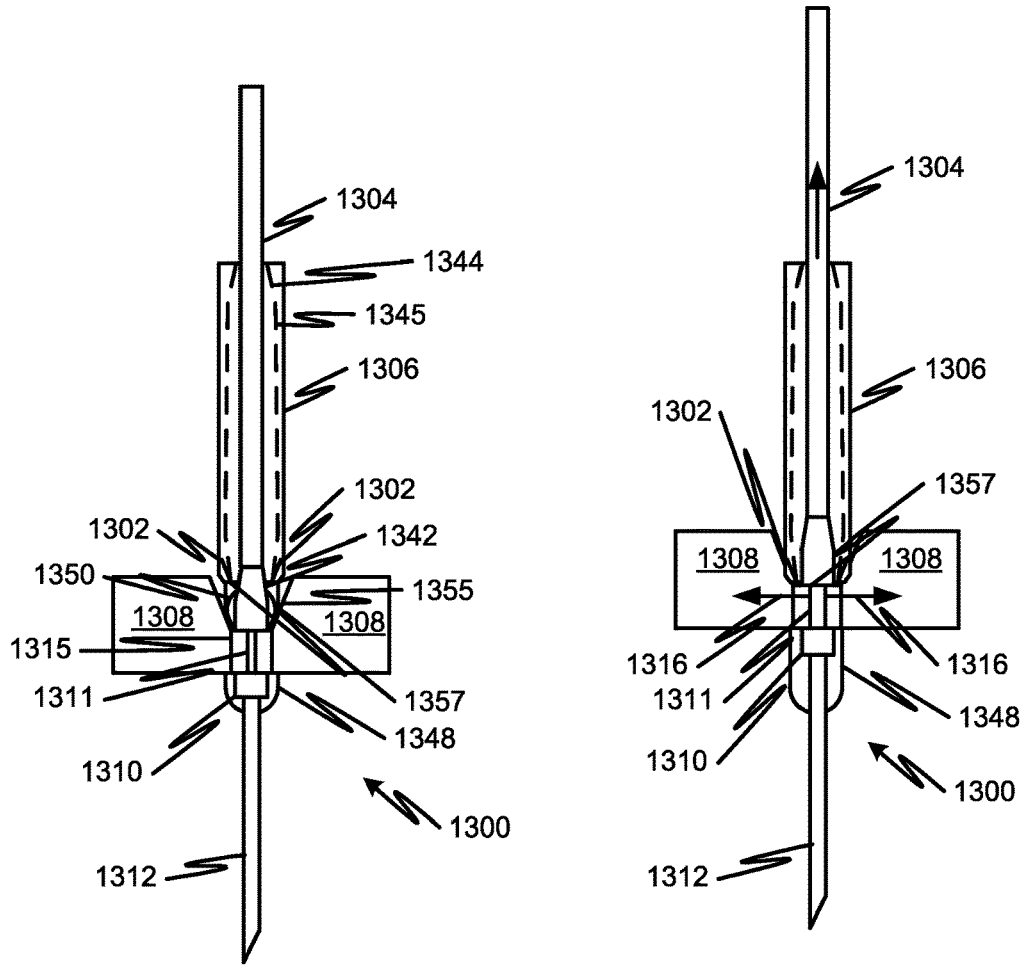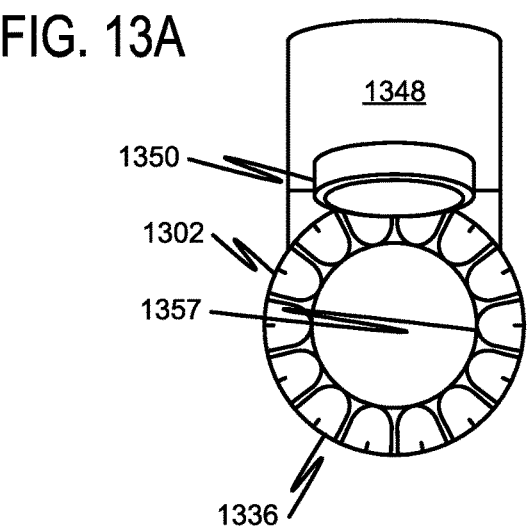
FIG. 13A  FIG. 13B
FIG. 13C

SAFE CANNULATION DEVICES, METHODS, AND SYSTEMS

CROSS-REFERENCE TO RELATED APPLICATIONS

The present application claims the benefit of U.S. Provisional Application No. 61/759,666, filed Feb. 1, 2013, which is hereby incorporated by reference herein in its entirety.

FIELD

The present disclosure relates generally to methods and devices for use and handling of intravenous and/or subcutaneous needles, and, more particularly, to safety devices for shielding a needles or other sharp articles or devices that present a safety hazard.

BACKGROUND

Needles and other sharp articles are widely used in hospitals and other patient care settings. A class of needles known as butterfly needles and associated shield devices are described in U.S. Pat. Nos. 5,112,311; 5,266,072; 5,433,703; 5,562,636; 5,562,637; 5,704,924; 5,772,638; 5,951,529; and 6,595,965.

SUMMARY

Methods and devices for use and handling of intravenous and/or subcutaneous needles, and, more particularly, to safety devices for shielding needles or other sharp articles or devices that present a safety hazard are disclosed. In an embodiment, a needle protective sheath can include a top wall, a bottom wall, and a pair of side walls joining the top and bottom walls. A finger shield extends from the top wall at a front opening of the sheath and is attached to the top wall by a hinge portion. The finger shield can be rotated (or folded) about the hinge portion to block the front opening so as to secure a cannula of the needle within the sheath.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIGS. 13A to 13C illustrate configurations in which wings of the butterfly needle can pop off the hub when the needle cannula is drawn into the protective sheath, according to embodiments of the disclosed subject matter.

DETAILED DESCRIPTION

Butterfly needles can be used for transfusions, in particular for taking a blood sample, or for providing a treatment to a patient, such as a dialysis treatment. In any of the embodiments, generally needles have a hub and a cannula and may include a tube with one or more connectors at a proximal end of the tube. The lumen of the cannula can be single or multiple and each may be in fluid communication with a respective tube. The cannula is commonly made of metal with a sharp tip but can be of other materials such as ceramic or plastic and may have a blunt tip as in a buttonhole needle. As the term is used here, needle can also encompass what many identify as a needle set which includes tubes, connectors, junctions, etc., for example, to facilitate the connection of the cannula to fluid circuits.

Figure 1:
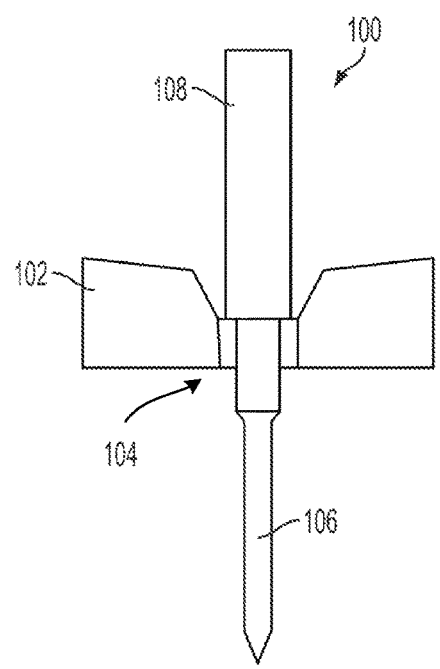
FIG. 1 shows a butterfly needle for insertion into a patient access, according to embodiments of the disclosed subject matter.

Many needles are termed butterfly needles on account of a pair of wings that extend radially from a hub of the needle. FIG. 1 shows an example of a butterfly needle 100. The needle 100 includes a cannula 106 for piercing the skin of a patient and for providing fluid communication between an opening on the cannula 106 and tubing 108. The cannula 106 may be of a single or multiple (e.g., dual) lumen type. Tubing 108 can connect to other tubing, machines, or fluid receptacles, such as a blood sample vacuum tube. Tubing 108 is connected to the cannula 106 by a hub 104. Hub 104 has a pair of wings 102 which extend radially from the hub. By pressing the wings 102 together, handling of the needle 100 for insertion into an access site of the patient is facilitated. Additionally or alternatively, the wings 102 can be taped to the patient to hold the needle 100 in position when inserted at the access site. Thus, the wings 102 are also referred to herein as taping wings.

Figure 2A:
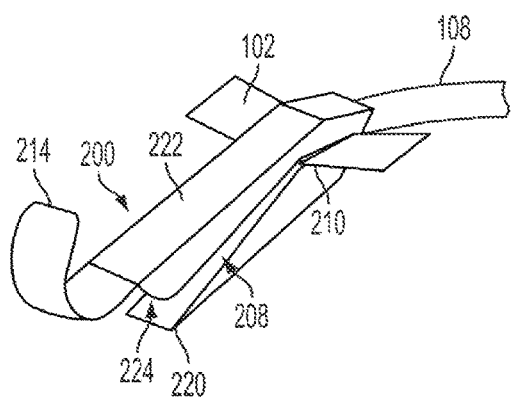
FIG. 2A is an isometric view of a needle protective sheath for use with a butterfly needle, according to one or more embodiments of the disclosed subject matter.
Figure 2B:
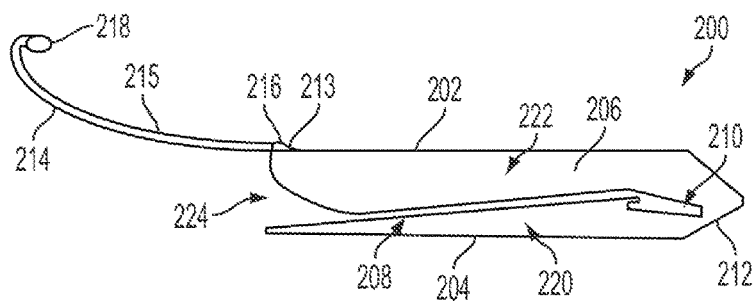
FIG. 2B is a side view of a needle protective sheath for use with a butterfly needle, according to one or more embodiments of the disclosed subject matter.

In one or more embodiments of the disclosed subject matter, a needle protective sheath 200, as shown in FIGS. 2A-2B, can fit over a needle 100 to receive the needle after removal from a patient access. The sheath 200 can have a top wall 202, a bottom wall 204, and a pair of side walls 206. The walls can define a front opening 224 at one end of the sheath 200 and a rear opening 212 at the other end of the sheath 200. The rear opening 212 can allow tubing 108 of the needle 100 to pass therethrough such that the sheath 200 can be coupled to the needle 100 when inserted into the patient access.

Each of the side walls 206 can include a groove 208 that starts at the front opening 224 and extends to a point removed from the rear opening 212. The groove 208 may thus divide the sheath into an upper jaw 222 (defined by the top wall 202 and upper portions of the side walls 206) and a lower jaw 220 (defined by the bottom wall 204 and lower portions of the side walls 206). Optionally, a needle securing recess 210 may be provided at an end of groove 208 remote from the front opening 224 for receiving and retaining portions of wings 102 and/or hub 104 of the needle 100. The sheath 200 can be sized and shaped such that the end of cannula 106 of the needle 100 is completely contained in the sheath 200 (i.e., within walls 202, 204, 206 and remote from the front opening 224).

A finger shield 214 can extend from the top wall 202 at the front opening 224. The finger shield 214 can have a finger contact surface 215, for example, for applying pressure to a patient access during removal of the needle. The finger shield 214 can be attached to the top wall 202 by a hinge portion 216. A connection portion 213 may extend from a surface of the top wall 202. The finger shield 214 may also curved at an end 218 thereof, for example, to assist in applying pressure during needle removal.

After removal from a patient access, the needle (at least the cannula 106 and hub 105) may be drawn into the needle protective sheath to protect patients, medical personnel and others from accidental exposure. In embodiments, the needle protective sheath can be advanced over the needle to encase the needle by drawing the cannula into the sheath. The sheath may allow the needle to be advanced during use. Among the disclosed embodiments are needle protective sheaths with slots to accommodate wings of winged needles. See, for example, U.S. Pat. No. 5,951,529 entitled "Needle Protector Sheath," which is incorporated herein by reference in its entirety, for details of a needle protective sheath and its use.

Despite the use of the needle protective sheath, it is possible that the needle may be accidentally displaced from the sheath thereby exposing patients, medical personnel, or others to accidental contact with the cannula 106. Moreover, while needle protective sheaths improve safety, some risk is posed if the needle is not fully retracted so that the cannula is completely shielded from potentially creating a puncture. Still further, risks are created by the possibility of a finger entering the end of the needle protective sheath to cause a puncture or scratch. Still further, there is a risk that tissue can inadvertently enter the front opening of the protective sheath when the needle is retracted therein. Accordingly, an end cap for the front opening of the needle protective sheath may provide an additional layer of protection against accidental needle punctures. In particular, the finger shield (e.g., shield 214 in FIGS. 2A-2B) can be rotated into contact with the walls of the protective sheath to serve as an end cap and effectively close off the front opening after removal of the needle from the patient access.

Figure 3A:
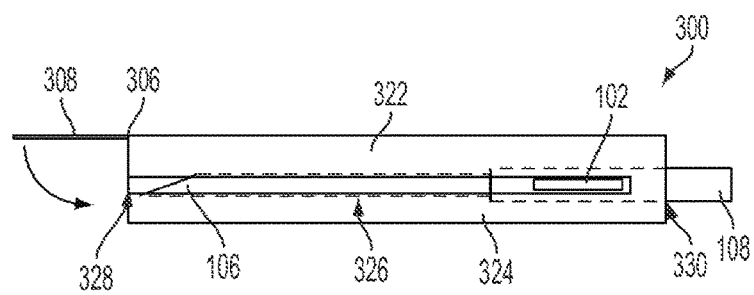
FIGS. 3A to 3B show side views of a needle protective sheath with a butterfly needle therein in open and secured configurations, respectively, according to embodiments of the disclosed subject matter.
Figure 3B:
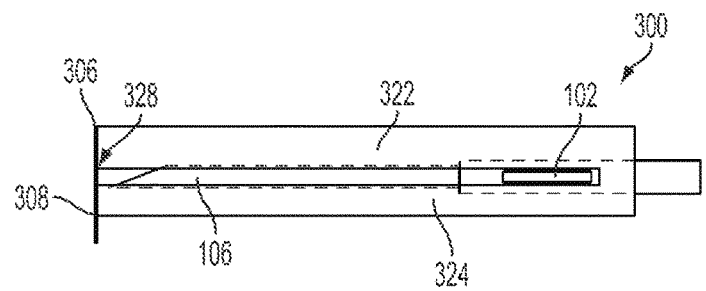

Referring to FIGS. 3A-3B, a needle protective sheath 300 with a needle retracted therein is shown. The needle protective sheath 300 has an upper jaw 322 and a lower jaw 324 separated by slot 326. Slot 326 is constructed to receive wings 102 of the needle therein as the needle is retracted into the sheath 300. Cannula 106 of the needle can be retracted into the sheath 300 by pulling on tubing 108, which extends through rear opening 330, until it is fully contained within the sheath 300, i.e., an end of the cannula 106 is displaced from the front opening 328. Finger shield 308 is connected to the upper jaw 322 by a bendable connection portion 306. The connection portion 306 can include, for example, a transverse groove to form a hinge or have a junction line for bending weakness. Once the cannula 106 is fully retracted into the protective sheath, finger shield 308 can be rotated about the connection portion 306 into contact with edges of the walls of the sheath at the front opening, thereby closing off the front opening and securing the needle therein.

Figure 3C:
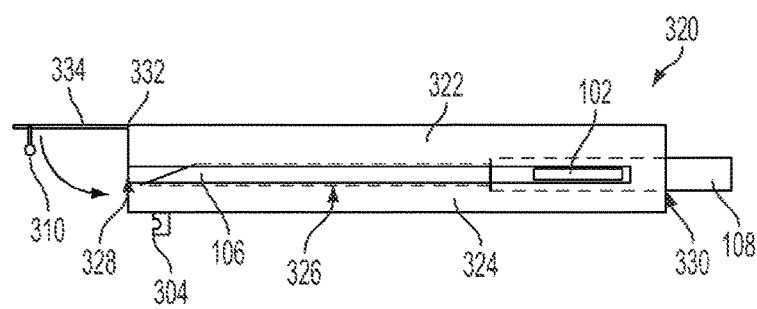
FIGS. 3C to 3D show side views of another needle protective sheath with a butterfly needle therein in open and secured configurations, respectively, according to embodiments of the disclosed subject matter.
Figure 3D:
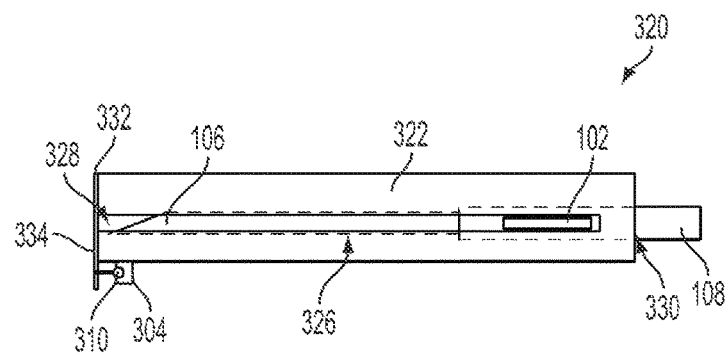

The needle protective sheath 320 can include one or more features to securely hold the finger shield to walls of the sheath to close the front opening 328 once the needle is retracted therein. For example, referring to FIGS. 3C-3D, a needle protective sheath 320 can include a finger shield 334 attached to an upper jaw 322 of the sheath by a bendable connection portion 332. The finger shield 334 can include a protrusion 310 extending from a surface thereof that is received by a receptacle 304 on the bottom jaw 324. Alternatively or additionally, the bottom and/or side walls can include a protrusion or latch while the finger shield includes an opening or receptacle for receiving the protrusion or latch therein. The finger shield 334 can thus be held at the front opening so as to secure the needle within the sheath.

Figure 4A:
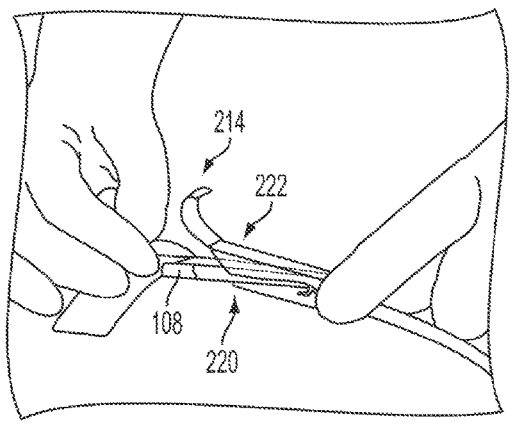
FIGS. 4A to 4F illustrate use of a needle protective sheath, according to embodiments of the disclosed subject matter.
Figure 4B:
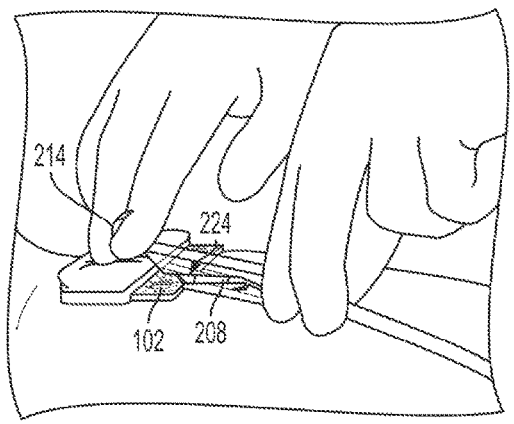
Figure 4C:
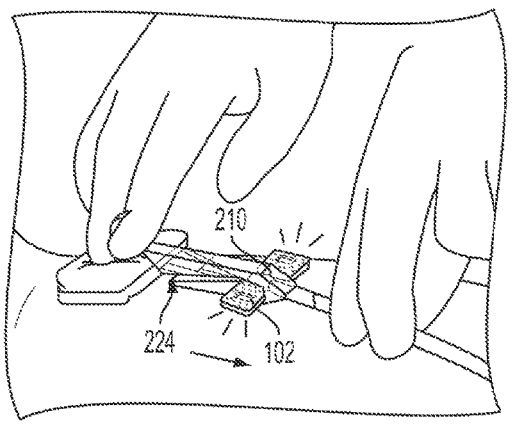
Figure 4D:
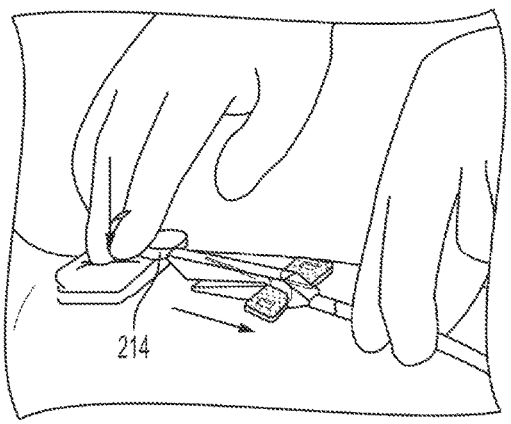
Figure 4E:
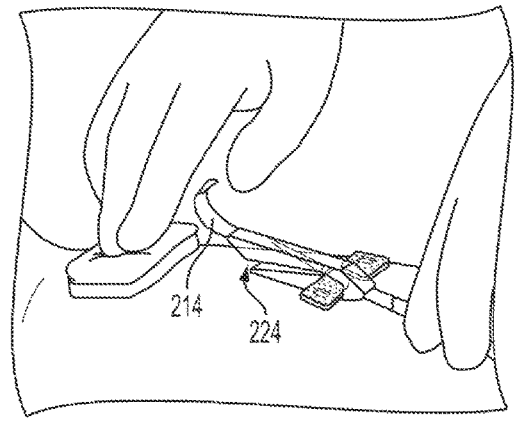
Figure 4F:
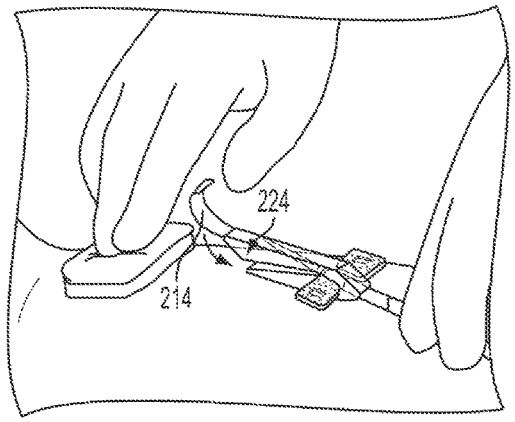

An exemplary use of the needle protective sheath is illustrated in FIGS. 4A-4F. The needle is inserted into a patient access, with the needle protective sheath at a rear end of the needle. Tubing 108 of the needle passes through the protective sheath. To remove the needle from the patient access, the needle protective sheath is moved into position adjacent the access site, as shown in FIG. 4B. Wings 102 of the needle proceed along the slot 208 between the upper jaw 222 and the lower jaw 220. The finger shield 214 is disposed over the patient access site and used to apply pressure to the site. At FIG. 4C, the needle is removed from the access site by pulling on tubing 108, thereby retracting the needle into the sheath. The needle wings 102 may be pulled into engagement with a recess at a rear portion of slot 208 in order to secure the needle in the protective sheath. The needle protective sheath can then be pulled away from the patient access site while continuing to apply finger pressure to the access site by way of finger shield 214, as shown in FIGS. 4D-4E. Once displaced from the access site, the finger shield 214 may be rotated into engagement with the walls of the needle protective sheath so as to close the front opening 224, thereby securing the needle within the protective sheath.

Figure 5A:
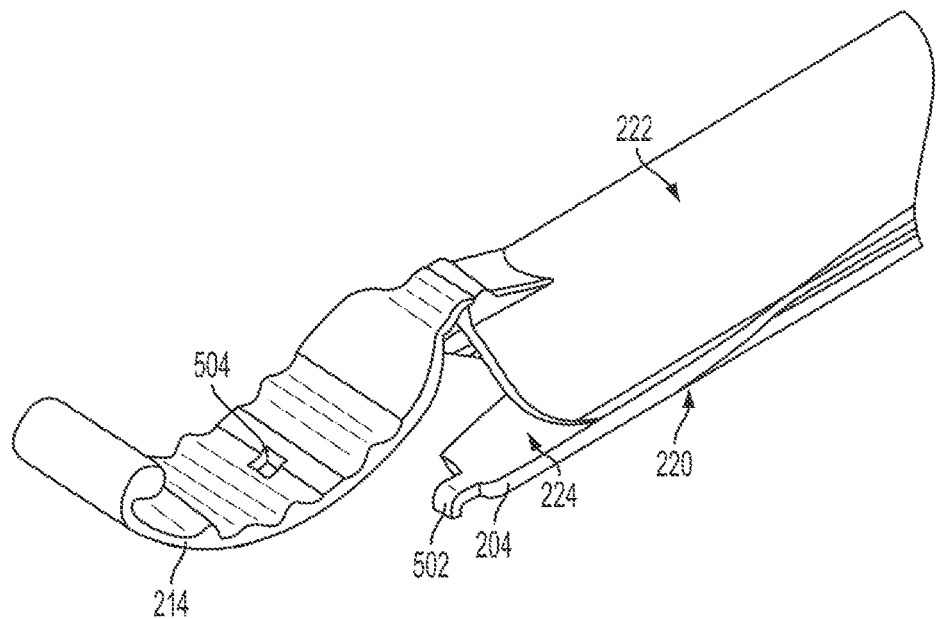
FIGS. 5A to 5B are isometric views of a needle protective sheath in open and secured configurations, respectively, according to embodiments of the disclosed subject matter.
Figure 5B:
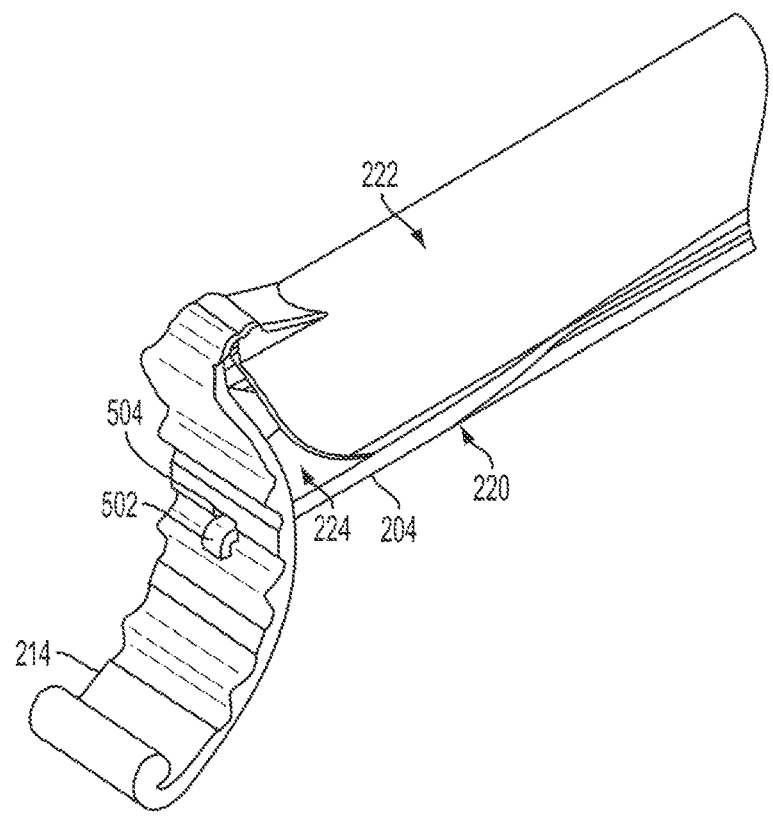

Various mechanisms for engagement between the rotated finger shield and the needle protective sheath walls at the front opening are possible according to one or more contemplated embodiments. For example, FIGS. 5A-5B show a needle protective sheath using a latch that grasps an opening. Finger shield 214 includes an opening 504 arranged to receive a latch 502 extending from bottom wall 204 at the front opening 224. Alternatively, the opening may be provided in a portion of the bottom and/or side walls while the latch is provided on the finger shield. The finger shield can have fraction features to prevent, or at least reduce the risk of, slipping when being manipulated by a user. For example, multiple ridges can be provided in the surface of the finger shield 214, as illustrated in FIGS. 5A-5B.

The latch 502 may snap into the opening 504 to secure the finger shield 214 at the opening 224. The latch 502 and opening 504 can be constructed so as to permanently secure the finger shield at the front opening, i.e., to prevent removal of the needle of the sheath. Alternatively, the latch 502 may be configured to be displaced from the opening 504 by appropriate manipulation to allow removal of the finger shield away from the front opening.

Figure 6A:
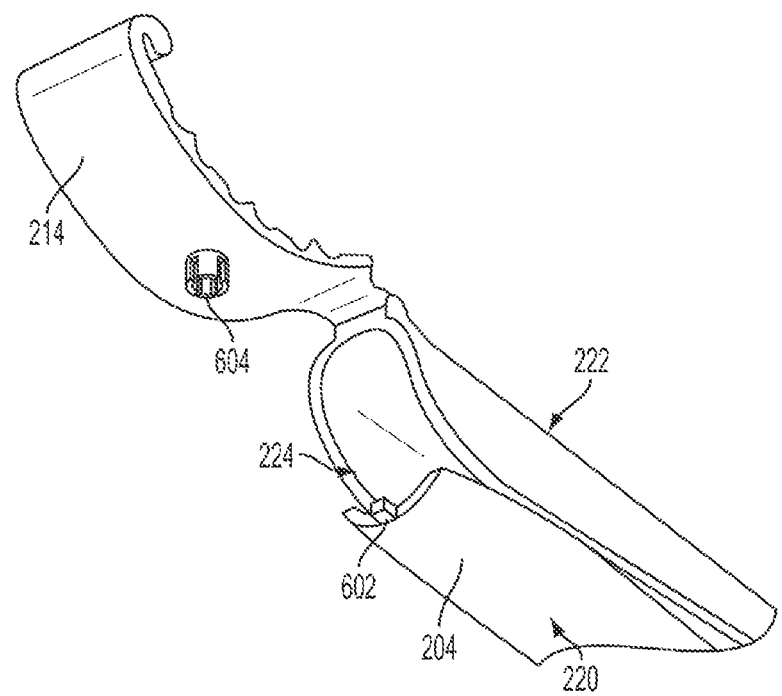
FIGS. 6A to 6B are isometric and side views of another needle protective sheath in open and secured configurations, respectively, according to embodiments of the disclosed subject matter.
Figure 6B:
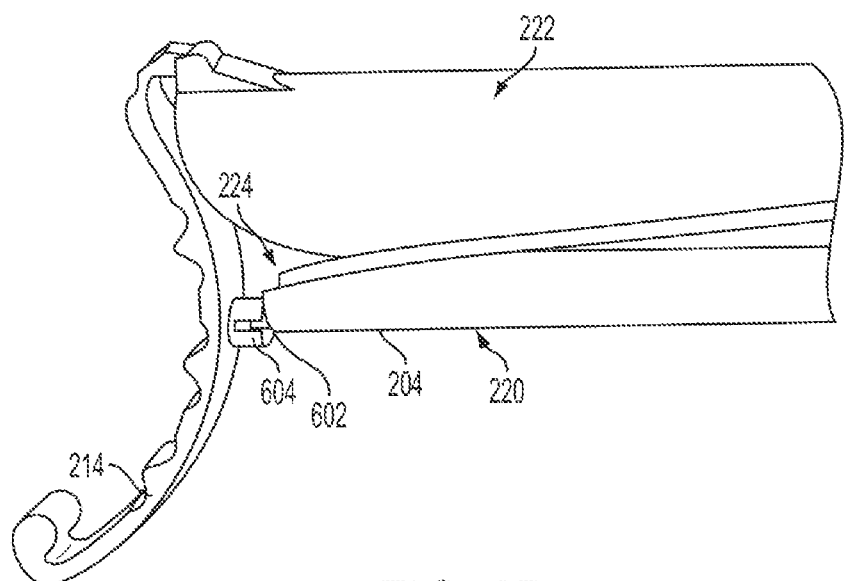
Figure 8A:
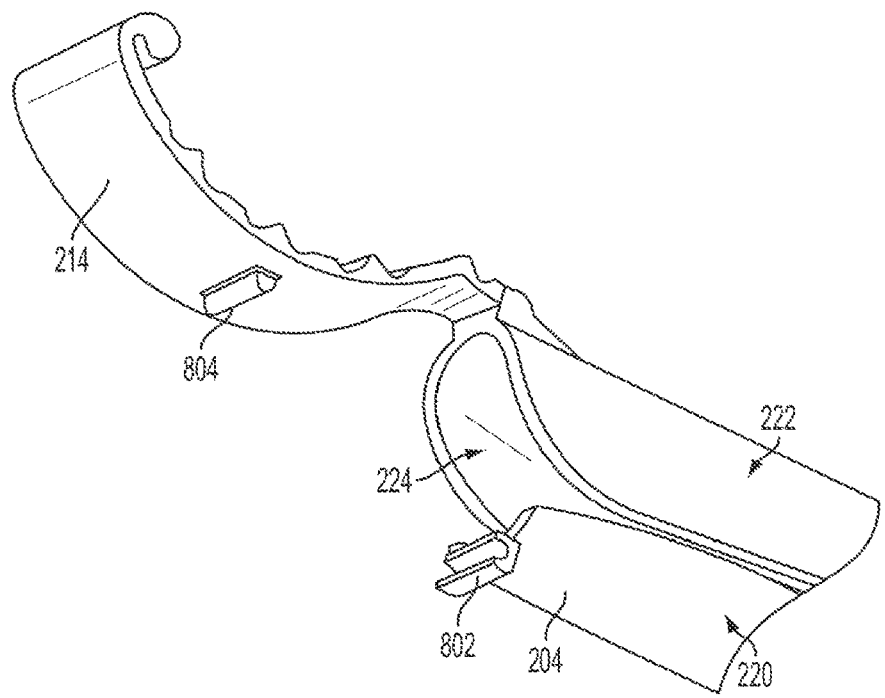
FIGS. 8A to 8B are isometric and side views of a fourth needle protective sheath in open and secured configurations, respectively, according to embodiments of the disclosed subject matter.
Figure 8B:
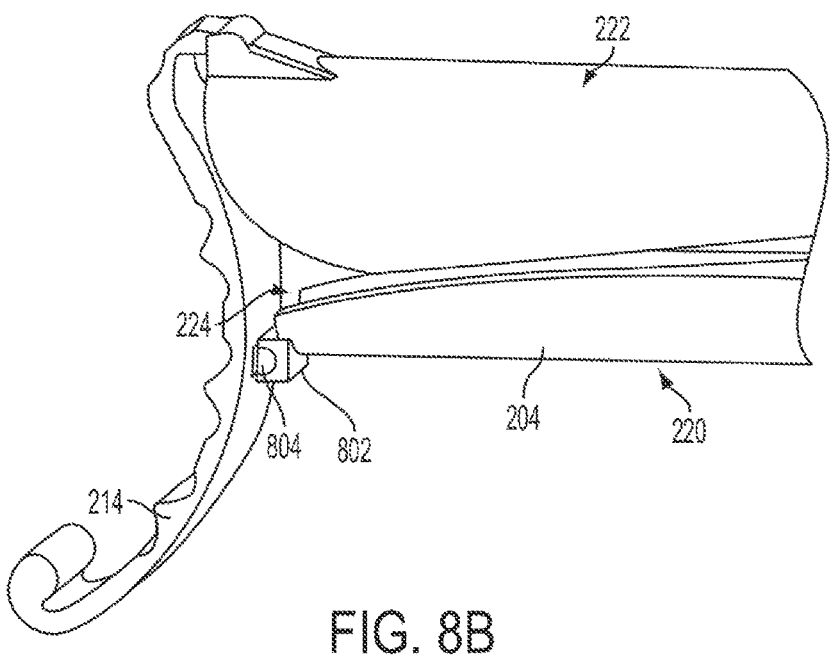

In another embodiment, the finger shield 214 can include a female securing receptacle 604 while the bottom wall 204 of the needle protective sheath can include a male locking peg or protrusion 602, as shown in FIGS. 6A-6B. The female securing receptacle 604 can receive the male locking peg 602 to secure the finger shield 214 at the opening 224. The peg 602 and receptacle 604 may form a friction fit with each other to reliably hold the two together. Alternatively or additionally, the receptacle can be provided on the bottom and/or side walls while the protrusion is provide on the finger shield. For example, a cylindrical protrusion 804 can be provided on a surface of the finger shield for coupling to a receptacle 802 at the bottom wall 204, as shown in FIGS. 8A-8B.

Figure 7A:
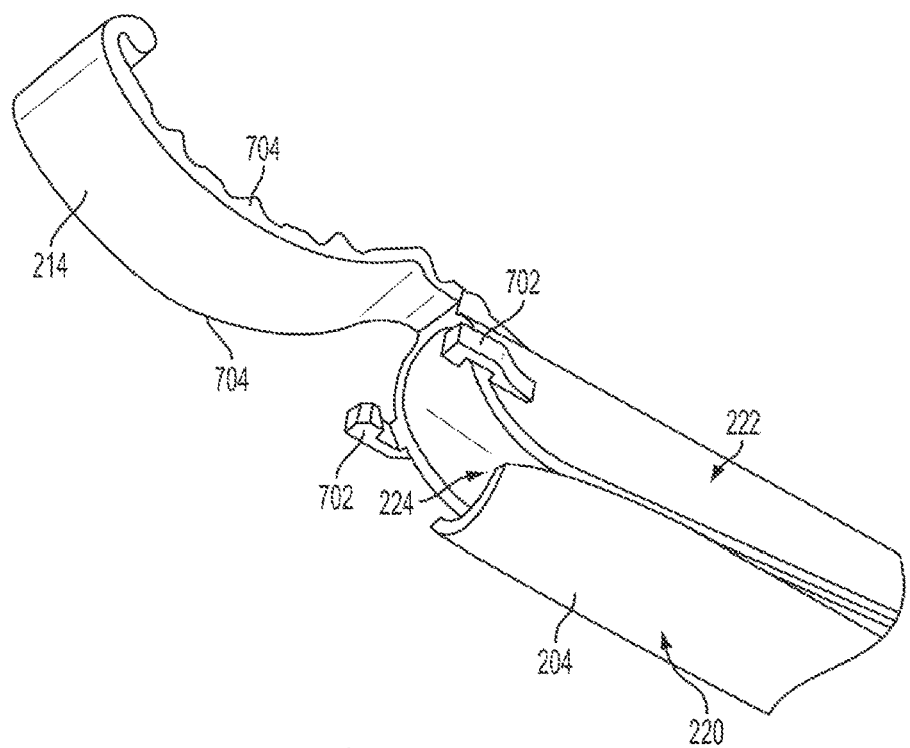
FIGS. 7A to 7B are isometric views of a third needle protective sheath in open and secured configurations, respectively, according to embodiments of the disclosed subject matter.
Figure 7B:
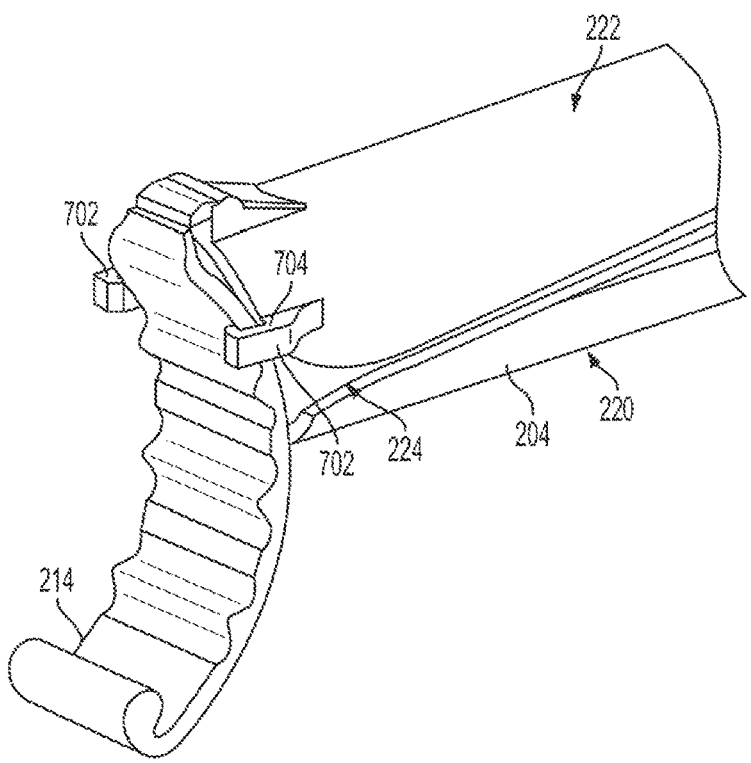

In another embodiment, the upper jaw 222 can include latch arms 702 on side walls of the needle protective sheath, as shown in FIGS. 7A-7B. The side wall latch arms 702 can be constructed to receive side portions 704 of the finger shield 214. For example, the finger shield 214 may snap into position and be held in place by the latch arms 702 at the front opening 224. Alternatively or additionally, the latch arms can be provided on the finger shield 214 for engaging portions of the side walls and/or bottom wall of the needle protective sheath. Alternatively or additionally, the latch arms 702 can be provided on lower jaw 220 or portions of bottom wall 204.

Figure 9A:
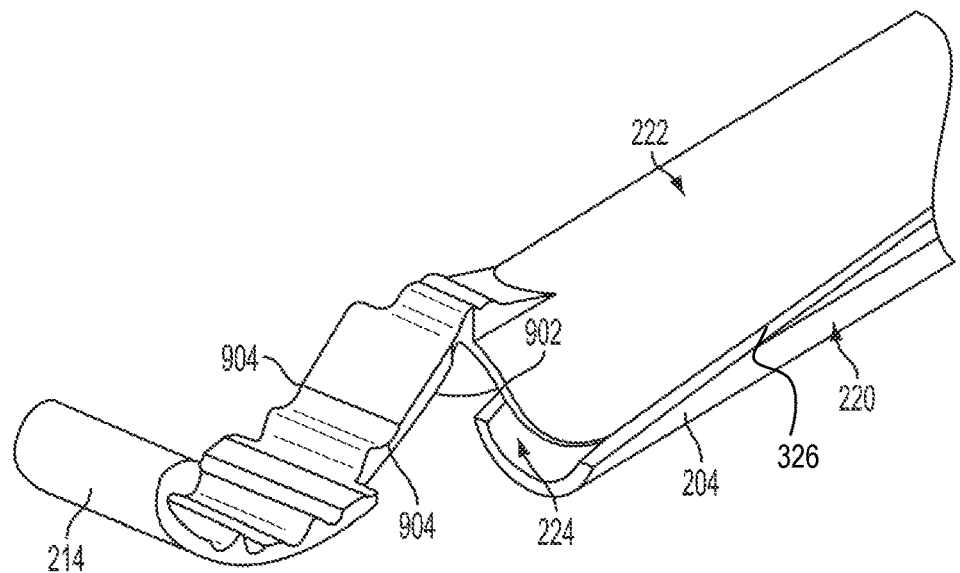
FIGS. 9A to 9B are isometric views of a fifth needle protective sheath in open and secured configurations, respectively, according to embodiments of the disclosed subject matter.
Figure 9B:
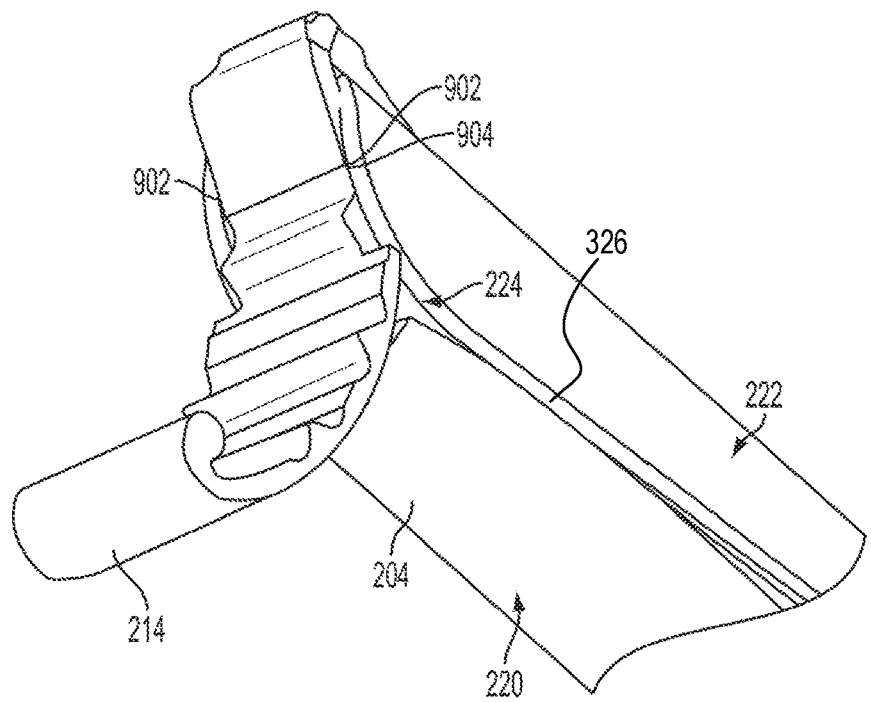

In yet another embodiment, the walls of the needle protective sheath may interact with portions of the finger shield 214 to secure the finger shield 214 at the front opening 224. For example, the finger shield 214 can have be sized and shaped to fit into the front opening 224, such that edge portions 904 of the finger shield 214 can interact with an interior face 902 of the upper jaw 222 to form a friction fit that retains the finger shield 214 in place at the front opening 224, as shown in FIGS. 9A-9B.

Figure 10A:
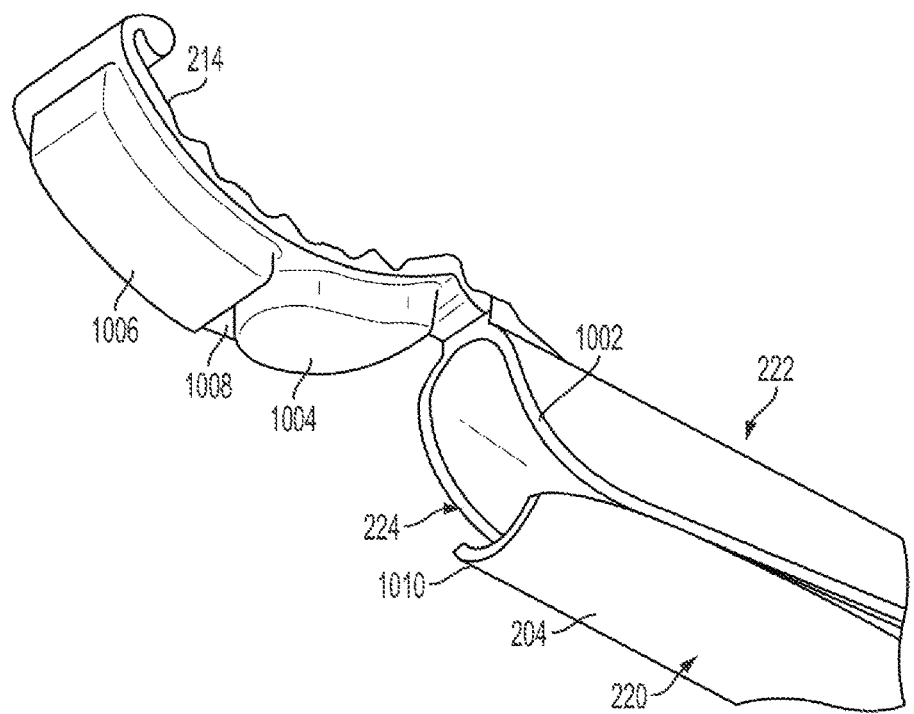
FIGS. 10A to 10B are isometric views of a sixth needle protective sheath in open and secured configurations, respectively, according to embodiments of the disclosed subject matter.
Figure 10B:
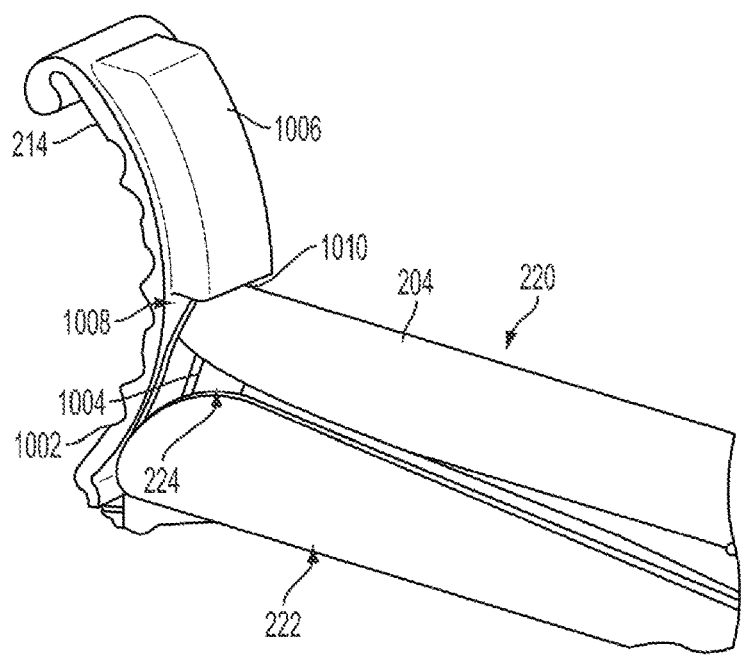

Alternatively or additionally, the finger shield 214 can be formed with one or more protrusions to fit into the front opening 224, as shown in FIGS. 10A-10B. Finger shield 214 can have an undersurface opening seal portion 1004 (i.e., first protrusion) constructed to fit into the front opening 224 when the finger shield is rotated. In addition, finger shield 214 can have an undersurface protrusion 1006 (i.e., second protrusion) separated from the seal portion 1004 by a gap 1008. The gap 1008 may be sized and shaped so as to receive bottom edge 1010 of the bottom jaw 204. Optionally, the seal portion 1004 may be sized and shaped to form a friction fit with one or more edges of the walls of the needle protective sheath, for example, edges 1002 of the upper jaw 222. Alternatively or additionally, the seal portion 1004 and protrusion 1006 can form a friction fit at the bottom edge 1010.

Of course, any of the features of the needle protective sheaths described above or elsewhere herein may be altered or combined to form additional embodiments of the needle protective sheath. For example, a needle protective sheath may include more than one of the mechanisms described with respect to FIGS. 3A-3D and 5A-10B for securing the finger shield in a closed position at the front opening of the needle protective sheath.

Figure 11A:
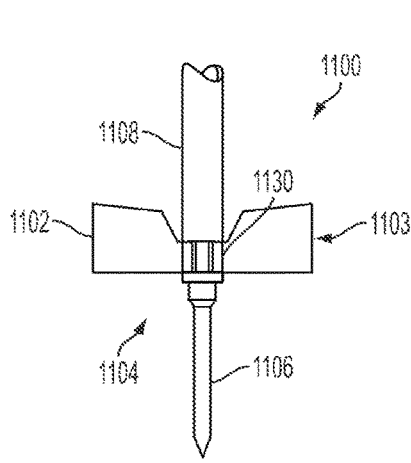
FIGS. 11A to 11H illustrate various views of a needle, needle protective sheath, and related components and features according to embodiments of the disclosed subject matter.
Figure 11B:
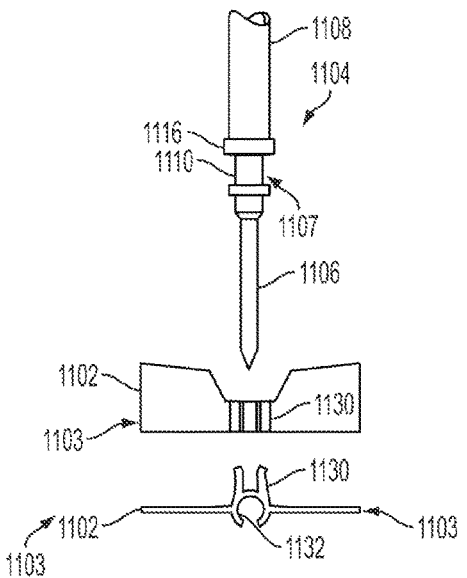

FIGS. 11A to 11H illustrate a needle, needle sheath, and related components and features according to embodiments of the disclosed subject matter. Referring to FIG. 11A, a needle 1100 has a removable grip portion (removable from the needle portion indicated at 1104), in the present embodiment in the form of pair of wings, one of which is indicated at 1102. A tubing portion 1108 connects to one or more lumens of a cannula 1106, which may be of a single or multiple (e.g., dual) lumen type. The grip portion 1103 is shown FIG. 11B with the grip portion 1103 (shown in side and profile views) separated from the needle portion 1104. A pair of releasing elements 1130 may be gripped and squeezed together to facilitate release of the grip portion 1103 from the needle portion 1104. An engagement portion 1110 of a needle hub 1107 may be shaped to locate the grip portion 1103 when attached to the hub portion 1107, in the present case by snapping engagement. This locates the grip portion 1103 in the axial direction and helps to ensure it is not accidentally shifted during use or placed at the incorrect part of the needle portion 1104.

Figure 11C:
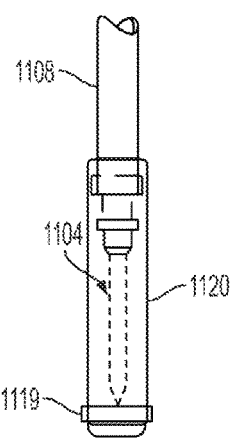
Figure 11D:
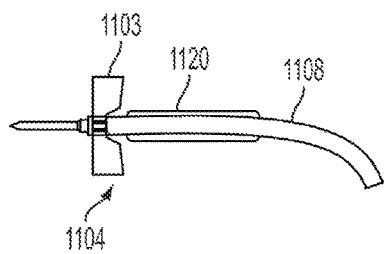
Figure 11E:
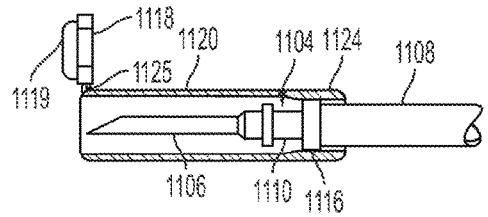
Figure 11F:
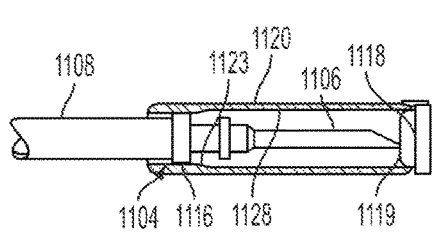
Figure 11G:
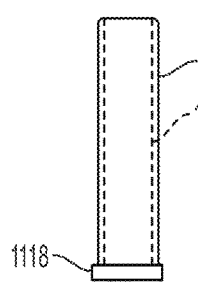
Figure 11H:
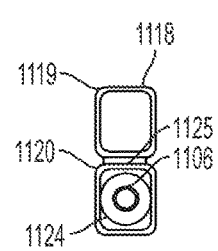

FIGS. 11C, 11E, and 11F show the needle portion 1104 enclosed within a protective sheath 1120. The protective sheath 1120 has a closeable cover 1118 that seals the protective sheath 1120 at a distal end thereof. The proximal end of the sheath 1120 is shaped to form a seal 1124 with a proximal portion 1116 of the needle portion 1104 when the latter is retracted into the sheath 1120. When the needle portion 1104 is retracted into the sheath 1120, the closeable cover 1118 can be closed and sealed. To allow the closeable cover 1118 to seal, a sealing portion such as a plug 1119 may be provided. The plug 1119 may be configured along with the needle portion 1104 and the sheath 1120 such that the plug pushes the needle portion proximal portion 1116 into sealing engagement with the sheath proximal end seal 1124. The sheath proximal end narrows progressively, as indicated for example at 1123 in FIG. 11F, so that pushing the closeable cover 1118 closed may force the needle portion proximal portion 1116 into a tight seal with the sheath proximal end seal 1124. The cross-sectional shape of the seal 1124 at the sheath proximal end may be formed to match that of the needle portion proximal portion 1116. The closeable cover 1118 may be attached by means of a living hinge 1125. In embodiments, the seal 1124 has a circular cross-section. FIG. 11H shows an end view of the needle 1104 and inserted in the protective sheath 1120 (with the closeable cover 1118 open) at the center.

A view of the needle 1100 disassembled (into needle portion 1104 and grip portion 1103) is shown at 11B. The needle 1104 section left side enclosed within the sheath 1120 with the sheath closeable cover 1118 closed is shown at FIG. 11F. The needle 1104 section right side enclosed within the sheath 1120 with the sheath closeable cover 1118 open is shown at FIG. 11E. FIG. 11G shows the sheath 1120 with its inner walls 1128 indicated in phantom. FIG. 11C shows the needle portion 1104 (after the grip portion 1103 has been detached) with the cannula 1106 sealed within the closed sheath 1120. In this configuration, any leakage from the needle portion 1104 is fully sealed within an interior volume of the sheath 1120 because the latter is sealed at both ends thereof with seals formed at distal and proximal ends of the needle portion 1104.

FIG. 11D shows the needle 1100 extending out of the sheath 1120 with the sheath being held in alignment for receiving the needle portion 1104 after the grip portion 1103 is removed. In use, a kit can be provided as shown in FIG. 11D, which includes the needle 1100 with the removable grip portion 1103 installed on the needle portion 1104 and the protective sheath 1120 held on the tubing 1108 by virtue of the latter being inserted through the open internal volume of the protective sheath 1120. A channel for the tubing 1108 is defined because the sheath distal end is open and the proximal end is sealed by the needle proximal portion 1106 itself. Note that the cover 1118 can be provided with an extension on a side opposite a connection to the protective sheath 1120 (e.g., living hinge 1125) which can be gripped by a user to hold the protective sheath 1120 back as the needle portion 1104 is withdrawn into the protective sheath 1120 after removal of the grip portion.

Figure 12A:
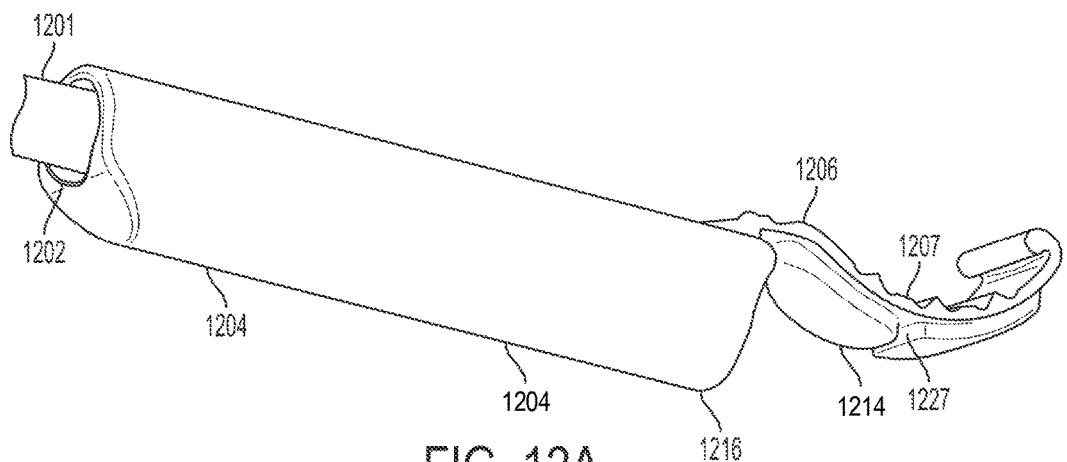
FIGS. 12A to 12E illustrate needle, needle protective sheath, and related components and features, according to further embodiments of the disclosed subject matter.
Figure 12B:
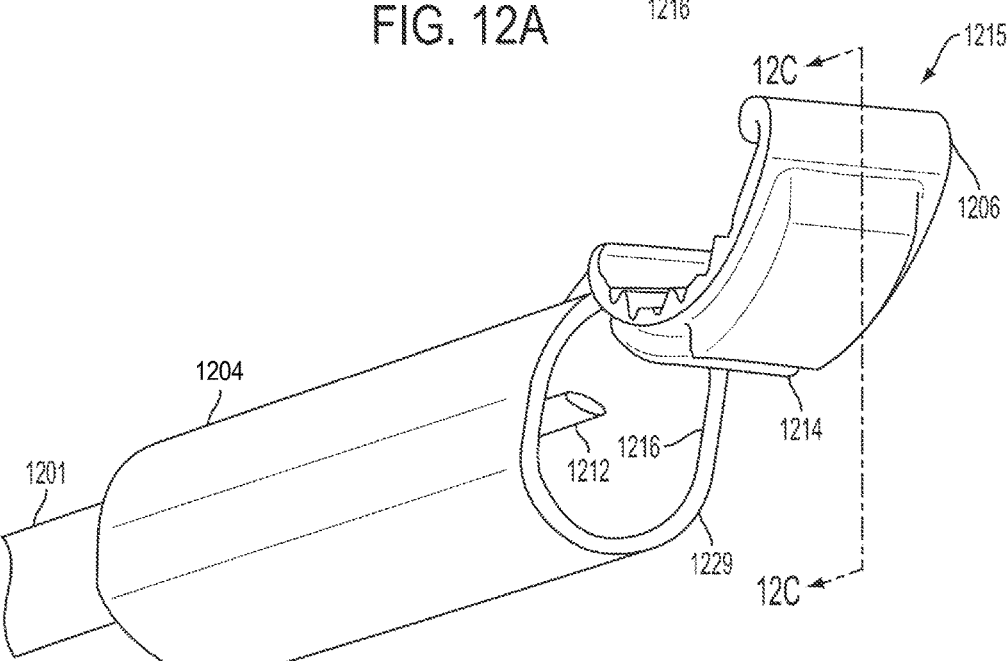
Figure 12C:
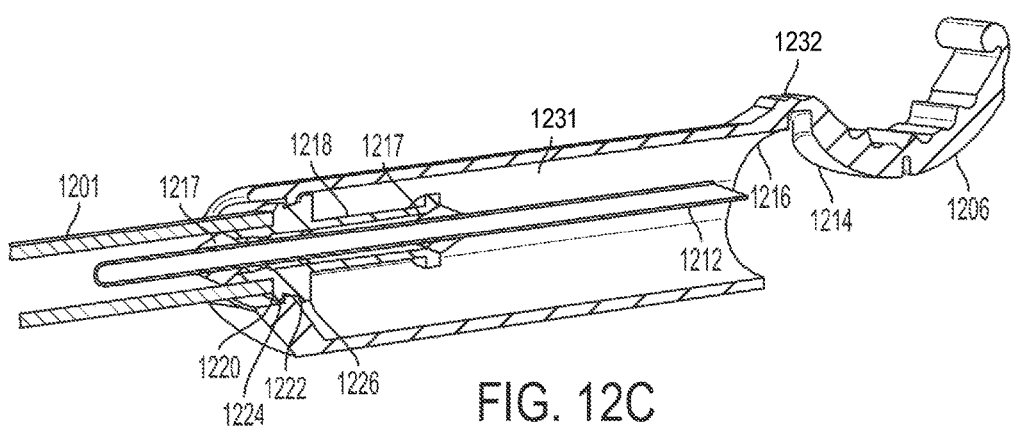

In a method, the following steps can be performed:
1. A needle 1100 is provided with a detachable grip portion 1103, needle portion 1104, and a connected protective sheath 1120, where the sheath is slidable along a tubing 1108 that allows fluid to flow into one or more lumens of the needle 1100. The protective sheath is sealable at both ends, optionally using portions of the needle. The needle is extended or provided extended from the sheath. The needle may have a sterile tip guard enclosing it, as known in the art.
2. After removal of any optional tip guard, the needle is inserted in a patient and used. The sheath remains connected at the proximal end of the needle as shown in FIG. 11D. The grip portion 1103 may be used in the fashion of, for example, butterfly needles as known in the art.
3. Once the needle is to be extracted from the patient, the grip portion 1103 may be removed, for example, by pinching the releasing elements 1130 or by just prying the recess 1132 from the engagement portion 1110.
4. If present, the extension portion of the cover (See an example of an extension 1206 in a further embodiment illustrated in FIGS. 12A to 12C and attending discussion) can be held while the tubing 1108 is drawn proximally to pull the needle portion 1104 into the sheath 1120.
5. The needle portion 1104 or tubing 1108 is moved firmly to seal the needle proximal portion 1116 in the sheath proximal portion 1124 in order to make it possible to close the cover 1118 (e.g., finger shield). The cover 1118 is then closed, thereby sealing the distal end of the protective sheath 1120 and the proximal portion 1124 of the sheath 1120.

FIGS. 12A to 12E illustrate needle, needle protective sheath, and related components and features according to further embodiments of the disclosed subject matter. A protective sheath 1204 has a proximal end 1202 that forms a seal by means of a ridge 1224 of the protective sheath 1204 that fits into a channel 1222 of a needle hub 1218 bounded by flanges 1220 and 1226 of the hub 1218. This creates a combination of interference- and frictional-engagement that forms a fluid-tight seal at the proximal end 1202 of the protective sheath 1204. In alternative embodiments, the ridge and channel may switch between the sheath 1204 and hub 1218. The interference may also be such that the hub creates a palpable or audible indication of engagement to form the seal. The hub 1218 may be bonded with an epoxy material or thermosetting material as indicated at 1217. Tubing 1201 may be frictionally connected to the hub 1218 or attached according to any known methods. A cannula 1212 of the needle fits into an internal volume 1231 of the protective sheath 1204.

A cover 1215 with an extension portion 1206 is integrally attached by a living hinge 1232 to the protective sheath 1204. The cover 1215 also has a plug shaped feature 1214 that fits into a distal opening 1216 of the sheath 1204 to seal it when the cover 1215 is closed. The cover 1215 may have a more flexible region 1207 at the base of the extension portion 1206 so that when the cover 1215 is closed, the extension portion can yield when pressure is inadvertently applied to it which might otherwise cause the plug shaped feature 1214 to unseal. Also, the cover 1215 is curved in a way that makes it less likely to catch on something, such as an article of clothing, which would cause it to open after being closed. The shape of the gap 1227 at the more flexible region 1207 wraps around the edge 1229 of the distal opening 1216 helping to ensure the cover resists reopening after closure.

Figure 12D:
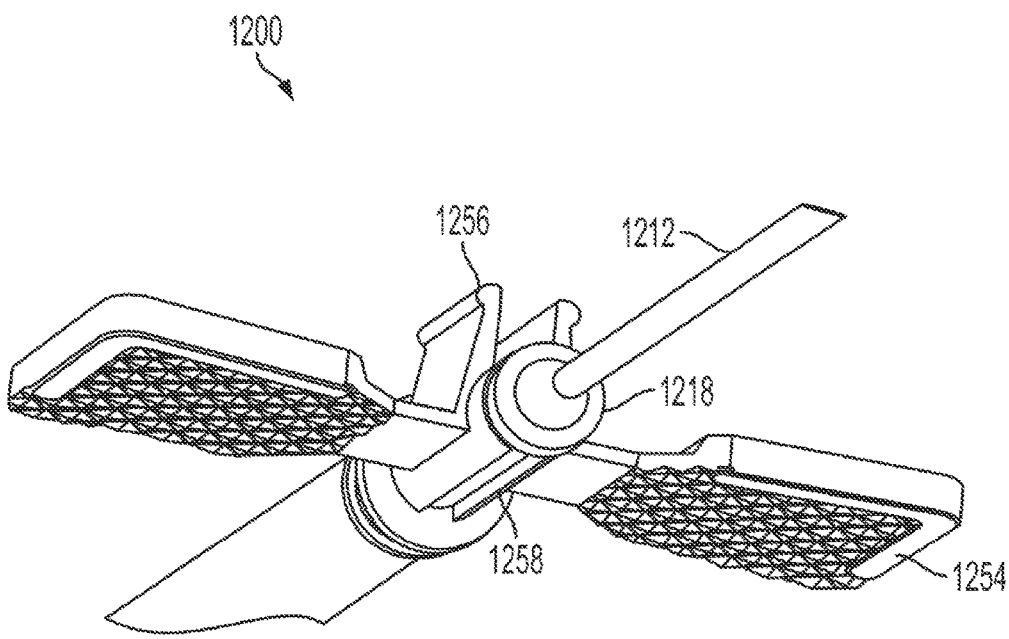
Figure 12E:
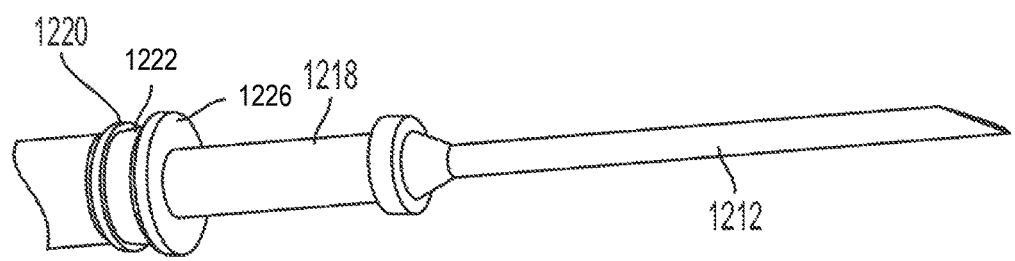

The needle with removable wing-type grip portion is shown at 1200 in FIG. 12D. The needle 1200 has a hub 1218, to which the grip portion is removably attached, and a cannula 1212. The hub 1218 can slide out a gap 1258 in the grip portion, which sliding may be facilitated by using releasing elements 1256 (which function as levers, as do releasing elements 1130 in FIGS. 11A-11B) to increase the open size of the gap 1258. The releasing elements 1256 are pinched together which leverages open the gap 1258 to facilitates release and reattachment of the grip portion 1254.

The functional features of the present embodiments of FIGS. 12A to 12E, as should be immediately apparent, may be as described with reference to the embodiments of FIGS. 11A through 11H including the method of use in described in the enumerated list above.

FIGS. 13A to 13C illustrate embodiments in which the wings are configured to pop off the hub when the needle is drawn into the protective sheath. A hub 1310 is attached to a cannula 1312 to form a needle 1300 which fits into a protective sheath 1306. The protective sheath 1306 has an interior volume 1345 with a tapered portion 1344 at its distal end that forms a compression seal with a similarly tapered portion 1342 of the hub 1310. A tube 1304 is attached to the hub 1310. When the tube 1304 is pulled relative to the protective sheath 1306, the tapered portions 1344 and 1342 are wedged together to form a tight seal. A finger shield carries a plug portion 1350 (see FIG. 13C) that seals the distal end of the protective sheath 1306 when a user folds the finger shield 1348 downwardly over the protective sheath 1306 after drawing the needle fully thereinto. Note that the features of the embodiment of FIG. 12C that provide a palpable click to confirm that the seal at the distal end has been properly formed can be incorporated in the present embodiment or others disclosed herein.

The hub 1310 has wings 1308 that are held on the hub 1310 by a clip 1315 that operates in the clip-on manner illustrated in, and discussed with reference to, FIGS. 11A-11B, 12D, and 12E, with clip-on engagement portions that form an interfering engagement between the wings 1308 and the hub 1310. In the present embodiment, the gap 1311 of the clip 1315 spreads apart when the sloping portion 1355 of the wings 1308 fit into and engage notches 1302 of the protective sheath 1306. This generates a lateral force directed as indicated by the arrows 1316, causing the clip 1315 to spread and thereby the gap 1311 to open up to release the clip 1315 and attached wings 1308 from the hub. This allows the hub 1310 and cannula 1312 to be drawn into the protective sheath 1306 and the finger shield 1348 folded to place the plug portion 1350 into opening 1357 of the protective sheath 1306.

Notches 1302 may be arrayed about the opening 1357 formed in the distal end of the protective sheath 1306. The notches 1302 are shown in the distal end view of the protective sheath 1306 in FIG. 13C. The notches 1302 may be sized and shaped so that when the wings 1308 are received in them, their orientations and/or positions are controlled to ensure that the continued pulling of the tube 1304 causes the clip 1315 to expand thereby releasing the wings 1308 (together with the clip 1315). Thus the notches 1302 may prevent the wings from slipping to the side under the separating force 1316 caused by pulling the tube 1304.

Figure 14A:
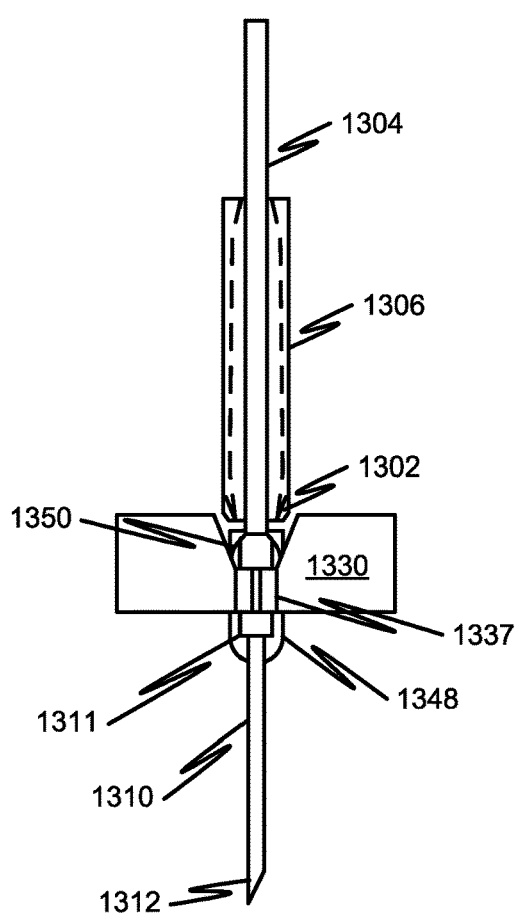
FIGS. 14A to 14C illustrate configurations in which wings of the butterfly needle can break or tear off the hub when the needle cannula is drawn into the protective sheath, according to embodiments of the disclosed subject matter.
Figure 14B:
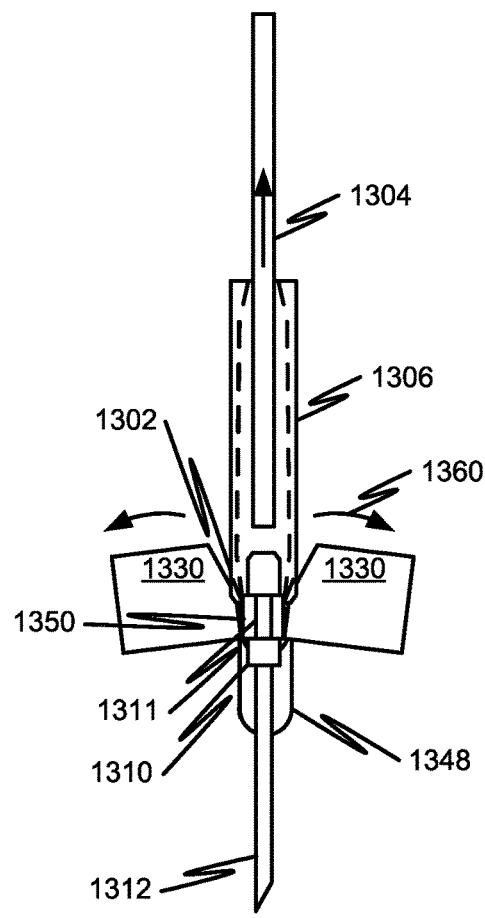
Figure 14C:
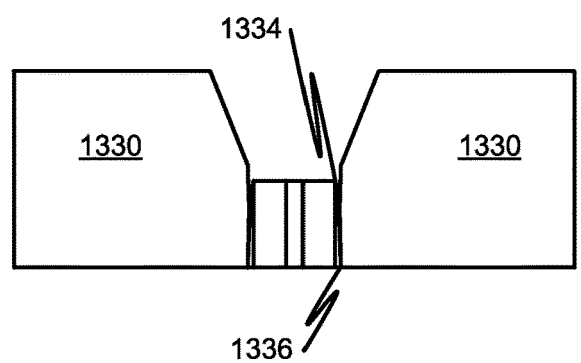

FIGS. 14A to 14C illustrate embodiments in which the wings are configured to break or tear off the hub when the needle is drawn into the sheath. The structures of the present embodiments can be identical to the structure of the embodiment of FIGS. 13A through 13C except that the wings 1330 are configured to be broken or torn from the hub 1311. The wings 1330 can have an intermediate member 1337 that attaches the wings to the hub 1311 such that they are held by interfering engagement or adhesive. Alternatively, the wings 1330 may be integral to the hub 1311. In any case, the wings 1330 may be attached to the intermediate member 1337 or the hub 1311 by a web or weakened material indicated at 1336 with a recess 1334 in FIG. 14C which may facilitate the breaking or tearing of the wing 1330 from the intermediate member 1337 or the hub 1311 when the tube 1304 is pulled. FIG. 14B shows the wings 1330 tilting, as indicated by the arrows 1360, down and away as the tube 1304 is pulled. Once the wings 1330 are removed, this allows the hub 1311 and cannula 1312 to be drawn into the protective sheath 1306 and the finger shield 1348 folded to place the plug portion 1350 into opening 1357 of the protective sheath 1306 (see FIGS. 13A and 13C for corresponding structure and reference numerals).

According to first embodiments thereof, a needle protective sheath comprises a top wall, a bottom wall, and a pair of side walls joining the top and bottom walls. In first embodiments, the walls define front and rear openings at opposite ends of the sheath. In first embodiments, each side wall has a slot therein extending from the front opening to a point displaced from the rear opening. In first embodiments, each slot is constructed to receive a wing extending from a hub of a butterfly needle as the needle is retracted into the needle protective sheath through the front opening. In first embodiments, the needle protective sheath further comprises a finger shield extending from the top wall at the front opening. In first embodiments, the finger shield is attached to the top wall by a hinge portion and is constructed to rotate about the hinge portion to block the front opening so as to secure the butterfly needle within the sheath.

Any of the foregoing first embodiments may be varied to form additional first embodiments in which the finger shield is constructed to rotate about the hinge portion and to contact the side walls. Any of the foregoing first embodiments may be varied to form additional first embodiments in which said contact between the finger shield and the side walls forms a friction fit. Any of the foregoing first embodiments may be varied to form additional first embodiments in which the finger shield includes a first projection extending from a surface thereof, the first projection being constructed to fit into the front opening to form a friction fit between the first projection and the walls. Any of the foregoing first embodiments may be varied to form additional first embodiments in which the finger shield includes first and second projections extending from a surface thereof, the first projection being separated from the second projection by a gap, the first projection being constructed to fit into the front opening, the gap being sized such that the bottom wall forms a friction fit with the first and second projections when a front edge of the bottom wall is disposed therein. Any of the foregoing first embodiments may be varied to form additional first embodiments in which at least one of the side and bottom walls includes a latch for engaging with a portion of the finger shield. Any of the foregoing first embodiments may be varied to form additional first embodiments in which one of the bottom wall and the finger shield includes a latch portion or protrusion, and the other of the bottom wall and the finger shield includes an opening or receptacle for receiving said latch portion or protrusion. Any of the foregoing first embodiments may be varied to form additional first embodiments in which each side wall includes a latch arm for securing the finger shield against the front opening.

According to second embodiments thereof, a cannulation device comprises a needle having a hub and a cannula. In second embodiments, the hub has a connection portion to which a grip portion is releasably attached. In second embodiments, the needle is connected to a tube. In second embodiments, the cannulation device further comprises a sheath having a channel therethrough sized to permit the tube to run through the channel and allow the sheath to be slid therealong up to and over the cannula. In second embodiments, the sheath is configured such that it is open only at proximal and distal ends thereof, the hub and sheath being shaped to form a fluid-tight seal when the hub is retracted into the proximal end. In second embodiments, the sheath has a cover portion attached to the sheath that can be closed to seal an opening at the distal end when the hub is retracted such that the cannula is fully enclosed when the hub is retracted and the cover portion is closed.

Any of the foregoing second embodiments may be varied to form additional second embodiments in which the cover portion is integral to the sheath. Any of the foregoing second embodiments may be varied to form additional second embodiments in which the cover portion has an extension forming a grip at a part of the cover portion that is remote from a portion by which it is attached to the sheath. Any of the foregoing second embodiments may be varied to form additional second embodiments in which the grip part has fraction features to prevent slipping. Any of the foregoing second embodiments may be varied to form additional second embodiments in which the traction features include multiple ridges. Any of the foregoing second embodiments may be varied to form additional second embodiments in which the hub has a sealing portion with a round cross-section whose diameter is larger than said tube, said sealing portion forming said seal at said proximal end. Any of the foregoing second embodiments may be varied to form additional second embodiments in which said sealing portion includes a channel which engages a ridge of said sheath to provide a combination of an interference and friction fit. Any of the foregoing second embodiments may be varied to form additional second embodiments in which said sealing portion includes a ridge which engages a channel of said sheath to provide a combination of an interference and friction fit. Any of the foregoing second embodiments may be varied to form additional second embodiments in which the hub and sheath are configured such that a making of said fluid-tight seal generates an audible or palpable signal.

According to third embodiments thereof, a cannulation device comprises a needle having a hub and a cannula, the hub having a connection portion to which a grip portion is releasably attached. In third embodiments, the needle is connected to a tube. In third embodiments, the cannulation device further comprises a sheath having a channel therethrough sized to permit the tube to run through the channel and allow the sheath to be slid therealong up to and over the cannula. In third embodiments, the sheath is configured such that it is open only at proximal and distal ends thereof, the hub and sheath being shaped to form a fluid-tight seal when the hub is retracted into the proximal end. In third embodiments, the sheath has a cover portion attachable to the sheath such as to seal an opening at the distal end when the hub is retracted such that the cannula is fully enclosed when the hub is retracted and the cover portion is closed.

Any of the foregoing third embodiments may be varied to form additional third embodiments in which the cover portion is integral to the sheath. Any of the foregoing third embodiments may be varied to form additional third embodiments in which the cover portion has an extension forming a grip at a part of the cover portion that is remote from a portion by which it is attached to the sheath. Any of the foregoing third embodiments may be varied to form additional third embodiments in which the grip part has traction features to prevent slipping. Any of the foregoing third embodiments may be varied to form additional third embodiments in which the traction features include multiple ridges. Any of the foregoing third embodiments may be varied to form additional third embodiments in which the hub has a sealing portion with a round cross-section whose diameter is larger than said tube, said sealing portion forming said seal at said proximal end. Any of the foregoing third embodiments may be varied to form additional third embodiments in which said sealing portion includes a channel which engages a ridge of said sheath to provide a combination of an interference and friction fit. Any of the foregoing third embodiments may be varied to form additional third embodiments in which said sealing portion includes a ridge which engages a channel of said sheath to provide a combination of an interference and friction fit. Any of the foregoing third embodiments may be varied to form additional third embodiments in which the hub and sheath are configured such that a making of said fluid-tight seal generates an audible or palpable signal.

According to fourth embodiments thereof, an access device comprises an access needle having a hub with detachable taping wings and a tube extending from the hub. In fourth embodiments, the tube is in fluid communication with a lumen of the needle through the hub. In fourth embodiments, the access device further comprises a protective sheath defining an inner enclosed volume with the tube slidably engaged therewithin such that the needle and/or hub can extend from a distal end of the protective sheath enclosed volume and the tube can extend from a proximal end, opposite the distal end, of the protective sheath enclosed volume. In fourth embodiments, the taping wings extend laterally away from the hub and are wider than a distal opening of the enclosed volume. In fourth embodiments, the access device further comprises a finger shield, being a flat or substantially flat member, integrally attached to and extending from a top side of the protective sheath distal end, the finger shield having an integral cover portion that closes over and covers said distal opening.

Any of the foregoing fourth embodiments may be varied to form additional fourth embodiments in which the cover portion has a first engagement portion and the protective sheath has a second engagement portion, the first and second engagement portions being configured to interferingly engage to hold the cover portion over the distal opening when closed thereover. Any of the foregoing fourth embodiments may be varied to form additional fourth embodiments in which the finger shield is flat in a lateral aspect and curved in an aspect orthogonal to the lateral aspect. Any of the foregoing fourth embodiments may be varied to form additional fourth embodiments in which the finger shield has ridges that are configured to engage the finger of a user when pressed by a user finger against the body of a patient to permit the protective sheath to be held in place against the body of the patient as the tube is drawn and the needle and needle hub pulled into the enclosed volume. Any of the foregoing fourth embodiments may be varied to form additional fourth embodiments in which the finger shield has ridges that are configured to engage the finger of a user when pressed by a user finger against the body of a patient to permit the protective sheath to be held in place against the body of the patient as the tube is drawn and the needle and needle hub pulled into the enclosed volume. Any of the foregoing fourth embodiments may be varied to form additional fourth embodiments in which said finger shield is shaped with a concave surface facing away from a longitudinal axis of the protective sheath. Any of the foregoing fourth embodiments may be varied to form additional fourth embodiments in which said finger shield is elongate with a lateral dimension that is smaller than a lateral dimension of the protective sheath. Any of the foregoing fourth embodiments may be varied to form additional fourth embodiments in which the protective sheath is generally cylindrical in shape. Any of the foregoing fourth embodiments may be varied to form additional fourth embodiments in which the integral cover portion and distal opening are shaped such that the cover portion can form a seal when it is closed thereover. Any of the foregoing fourth embodiments may be varied to form additional fourth embodiments in which the integral cover portion and distal opening are shaped such that the cover portion can form a seal, and the cover snaps into position due to interfering engagement upon forming a seal, when the finger shield is closed thereover. Any of the foregoing fourth embodiments may be varied to form additional fourth embodiments in which a living hinge is formed between the protective sheath and the finger shield.

According to fifth embodiments thereof, an access device comprises an access needle having a hub and a cannula, the hub having detachable taping wings and a tube extending from the hub. In fifth embodiments, the tube is in fluid communication with a lumen of the cannula through the hub. In fifth embodiments, the access device further comprises a protective sheath defining a channel with the tube slidably engaged therewithin such that the cannula and/or hub can extend from a distal end of the protective sheath channel and the tube can extend from a proximal end, opposite the distal end, of the protective sheath channel. In fifth embodiments, the taping wings extend laterally away from the hub and are wider than a distal opening of the channel. In fifth embodiments, the access device further comprises a finger shield, being a flat member, integrally attached to and extending from a top side of the protective sheath distal end, the finger shield having an integral cover portion that closes over and covers said distal opening.

Any of the foregoing fifth embodiments may be varied to form additional fifth embodiments in which the cover portion has a first engagement portion and the protective sheath has a second engagement portion, the first and second engagement portions being configured to interferingly engage to hold the cover portion over the distal opening when closed thereover to form a palpable snap engagement. Any of the foregoing fifth embodiments may be varied to form additional fifth embodiments in which the finger shield is flat in a lateral aspect and curved in an aspect orthogonal to the lateral aspect so that it curves away from the protective sheath longitudinal axis thereby to promote purchase of a user's finger when the protective sheath is pushed axially and the tube is drawn axially in an opposite direction of the push. Any of the foregoing fifth embodiments may be varied to form additional fifth embodiments in which the finger shield has ridges that are configured to engage the finger of a user when pressed by a user finger against the body of a patient to permit the protective sheath to be held in place against the body of the patient as the tube is drawn and the needle and needle hub pulled into the enclosed volume. Any of the foregoing fifth embodiments may be varied to form additional fifth embodiments in which the finger shield has ridges that are configured to engage the finger of a user when pressed by a user finger against the body of a patient to permit the protective sheath to be held in place against the body of the patient as the tube is drawn and the needle and needle hub pulled into the enclosed volume. Any of the foregoing fifth embodiments may be varied to form additional fifth embodiments in which said finger shield is shaped with a concave surface facing away from a longitudinal axis of the protective sheath. Any of the foregoing fifth embodiments may be varied to form additional fifth embodiments in which said finger shield is elongate with a lateral dimension that is smaller than a lateral dimension of the protective sheath. Any of the foregoing fifth embodiments may be varied to form additional fifth embodiments in which the protective sheath is generally cylindrical in shape. Any of the foregoing fifth embodiments may be varied to form additional fifth embodiments in which the integral cover portion and distal opening are shaped such that the cover portion can form a seal when it is closed thereover. Any of the foregoing fifth embodiments may be varied to form additional fifth embodiments in which the integral cover portion and distal opening are shaped such that the cover portion can form a seal, and the cover snaps into position due to interfering engagement upon forming a seal, when the finger shield is closed thereover. Any of the foregoing fifth embodiments may be varied to form additional fifth embodiments in which a living hinge is formed between the protective sheath and the finger shield. Any of the foregoing fifth embodiments may be varied to form additional fifth embodiments in which the finger shield is positioned so that when the protective sheath is positioned such that the needle hub is drawn thereinto with the needle partially extending from the protective sheath, the finger shield partially covers the needle such that as the needle is more fully drawn into the protective sheath, pressure may be applied on top of the needle enters a patient access without coming in direct contact with the needle once it emerges from the patient access. Any of the foregoing fifth embodiments may be varied to form additional fifth embodiments in which the taping wings are held on the hub by at least one of interfering and frictional engagement between the taping wings and the hub. Any of the foregoing fifth embodiments may be varied to form additional fifth embodiments in which the taping wings are held on the hub by both interfering and frictional engagement between the taping wings and the hub. Any of the foregoing fifth embodiments may be varied to form additional fifth embodiments in which the taping wings are held on the hub by interfering engagement between the taping wings and the hub. Any of the foregoing fifth embodiments may be varied to form additional fifth embodiments in which the taping wings are held on the hub by adhesive. Any of the foregoing fifth embodiments may be varied to form additional fifth embodiments in which the taping wings are held on the hub by a breakable bridge of material. Any of the foregoing fifth embodiments may be varied to form additional fifth embodiments in which the taping wings are held on the hub by a tearable web of material. Any of the foregoing fifth embodiments may be varied to form additional fifth embodiments in which the taping wings are held on the hub by a tearable web of material with a notch facing a proximal end of the hub to facilitate tearing of the web when the tube is pulled. Any of the foregoing fifth embodiments may be varied to form additional fifth embodiments in which the taping wings are held on the hub by a breakable bridge of material. Any of the foregoing fifth embodiments may be varied to form additional fifth embodiments in which the taping wings are held on the hub by a clamp portion that is openable to release the taping wings by pinching opposing tabs thereon.

According to sixth embodiments thereof, a method of cannulating a patient uses the device of any of the foregoing first through fifth embodiments. In sixth embodiments, the method comprises inserting a needle into a patient, and moving the protective sheath over the hub to position the finger shield over the point where the needle enters the patient. In sixth embodiments, the method further comprises holding the finger shield over the point where the needle enters the patient while withdrawing the cannula by pulling on a tube connected to the hub, thereby drawing the needle into the protective sheath, and folding the finger shield over the end of the protective sheath until it snaps into place such that the needle is captured inside said protective sheath.

Any of the foregoing sixth embodiments may be varied to form additional sixth embodiments in which the method further comprises supporting the finger shield by a living hinge at a distal end of the protective sheath. Any of the foregoing sixth embodiments may be varied to form additional sixth embodiments in which the method further comprises manually removing the taping wings from the hub by squeezing a pinching mechanism thereby to release an interference engagement of the taping wings with the hub. Any of the foregoing sixth embodiments may be varied to form additional sixth embodiments in which the method further comprises pulling the tube such that the taping wings engage leveraging portions thereon that are effective, in response to the pulling, to weaken an engagement of the taping wings with the hub such that the effect of the pulling is to cause the taping wings to be released, thereby allowing the needle to be drawn into the protective sheath.

According to seventh embodiments thereof, a method of cannulating a patient comprises inserting a needle with taping wings extending from a hub thereof into a patient and moving a protective sheath over the hub to position a finger shield over a point where the needle enters the patient. In seventh embodiments, the method further comprises holding the finger shield over the point where the needle enters the patient while withdrawing a cannula of the needle by pulling on a tube connected to the hub, thereby drawing the needle into the protective sheath, and folding the finger shield over the end of the protective sheath until it snaps into place such that the needle is captured inside said protective sheath.

Any of the foregoing seventh embodiments may be varied to form additional seventh embodiments in which the method further comprises supporting the finger shield by a living hinge at a distal end of the protective sheath. Any of the foregoing seventh embodiments may be varied to form additional seventh embodiments in which the method further comprises manually removing the taping wings from the hub by squeezing a pinching mechanism thereby to release an interference engagement of the taping wings with the hub. Any of the foregoing seventh embodiments may be varied to form additional seventh embodiments in which the method further comprises pulling the tube such that the taping wings of hub engage leveraging portions thereon that are effective, in response to the pulling, to weaken an engagement of the taping wings with the hub such that the effect of the pulling is to cause the taping wings to be released, thereby allowing the needle to be drawn into the protective sheath.

According to eighth embodiments thereof, an access device comprises an access needle having a hub, a cannula, and a flexible tube in fluid communication with a lumen of the cannula. In eighth embodiments, the access device further comprises a protective sheath defining a channel with the tube slidably engaged therewithin such that the cannula and/or hub can extend from a distal end of the protective sheath channel and the tube can extend from a proximal end, opposite the distal end, of the protective sheath channel. In eighth embodiments, the access device further comprises a finger shield, being a flat member, integrally attached to and extending from a top side of the protective sheath distal end. In eighth embodiments, the finger shield has an integral cover portion that closes over and covers said distal opening.

Any of the foregoing eighth embodiments may be varied to form additional eighth embodiments in which the cover portion has a first engagement portion and the protective sheath has a second engagement portion, the first and second engagement portions being configured to interferingly engage to hold the cover portion over the distal opening when closed thereover to form a palpable snap engagement. Any of the foregoing eighth embodiments may be varied to form additional eighth embodiments in which the finger shield is flat in a lateral aspect and curved in an aspect orthogonal to the lateral aspect so that it curves away from the protective sheath longitudinal axis. Any of the foregoing eighth embodiments may be varied to form additional eighth embodiments in which the finger shield has a traction portion that is configured to engage a finger of a user when pressed by the finger against the body of a patient to permit the protective sheath to be held in place against the body of the patient as the tube is drawn and the cannula and needle hub are pulled into the enclosed volume. Any of the foregoing eighth embodiments may be varied to form additional eighth embodiments in which the finger shield has ridges that are configured to engage a finger of a user when pressed by the finger against the body of a patient to permit the protective sheath to be held in place against the body of the patient as the tube is drawn and the cannula and needle hub are pulled into the enclosed volume. Any of the foregoing eighth embodiments may be varied to form additional eighth embodiments in which said finger shield is shaped with a concave surface facing away from a longitudinal axis of the protective sheath. Any of the foregoing eighth embodiments may be varied to form additional eighth embodiments in which said finger shield is elongate with a lateral dimension that is smaller than a lateral dimension of the protective sheath. Any of the foregoing eighth embodiments may be varied to form additional eighth embodiments in which the protective sheath is generally cylindrical in shape. Any of the foregoing eighth embodiments may be varied to form additional eighth embodiments in which the integral cover portion and distal opening are shaped such that the cover portion can form a seal when it is closed thereover. Any of the foregoing eighth embodiments may be varied to form additional eighth embodiments in which the integral cover portion and distal opening are shaped such that the cover portion can form a seal, and the cover snaps into position due to interfering engagement upon forming a seal, when the finger shield is closed thereover. Any of the foregoing eighth embodiments may be varied to form additional eighth embodiments in which a living hinge is formed between the protective sheath and the finger shield. Any of the foregoing eighth embodiments may be varied to form additional eighth embodiments in which the finger shield is positioned so that when the needle hub is drawn into the protective sheath with the cannula partially extending from the protective sheath, the finger shield partially covers the cannula such that as the needle is more fully drawn into the protective sheath, pressure may be applied on top of a patient access without coming in direct contact with the cannula once it emerges from the patient access.

In any of the embodiments, alternative embodiments can be formed in which a cover may be provided as a separate element. In certain embodiments the cover may be provided as part of the grip portion, for example by means of a plug formed in one or both wings of a suitably configured grip portion.

In any of the embodiments having wings, such as taping wings, the wings may be removed, along with accommodations for them such as slots in the sides of a protective sheath, to form alternative embodiments. In any of the embodiments with wings, the wings and/or protective sheath may be modified to permit the wings to fit into the protective sheath and any slots in the side of the wings may be removed from the embodiment so as to form further embodiments. In any of the embodiments with wings, the wings and/or protective sheath may be modified to cause the wings to fold and fit into the protective sheath when the proximal tube is drawn (correspondingly any slots in the side of the wings may be removed) so as to form further embodiments. Any of the proximal seal mechanisms by which the needle hub seals with a protective sheath may be interchanged to form new embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for safe cannulation. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A needle protective sheath, comprising:
a top wall, a bottom wall, and a pair of side walls joining the top and bottom walls,
the walls defining a front opening and a rear opening at opposite ends of the sheath,
each side wall having a slot therein extending from the front opening to a point displaced from the rear opening, each slot being constructed to receive a wing extending from a hub of a butterfly needle as the needle is retracted into the needle protective sheath through the front opening, and a finger shield extending from the top wall at the front opening, the finger shield being attached to the top wall by a hinge portion, the finger shield being constructed to rotate about the hinge portion, wherein the finger shield is configured to block the front opening when the finger shield is rotated about the hinge portion from an open position to a closed position so as to secure the butterfly needle within the sheath when the finger shield is in the closed position, the finger shield is configured to remain secured in the closed position after it is rotated about the hinge portion into the closed position, and the finger shield includes a first portion having a first width measured in a direction perpendicular to a longitudinal axis of the sheath that fits into the front opening, a second portion having a second width measured in said direction greater than the first width, and the second width not fitting into the front opening when the finger shield is in the closed position.

2. The sheath according to claim 1, wherein the first portion of the finger shield is immediately adjacent to the second portion of the finger shield.

3. A needle protective sheath, comprising:

a top wall, a bottom wall, and a pair of side walls joining the top and bottom walls, the walls defining a front opening and a rear opening at opposite ends of the sheath, each side wall having a slot therein extending from the front opening to a point displaced from the rear opening, each slot being constructed to receive a wing extending from a hub of a butterfly needle as the needle is retracted into the needle protective sheath through the front opening, and a finger shield extending from the top wall at the front opening, the finger shield being attached to the top wall by a hinge portion, the finger shield being constructed to rotate about the hinge portion, wherein the finger shield is configured to block the front opening when the finger shield is rotated about the hinge portion from an open position to a closed position so as to secure the butterfly needle within the sheath when the finger shield is in the closed position, the finger shield is configured to remain secured in the closed position after it is rotated about the hinge portion into the closed position, the finger shield is constructed to rotate about the hinge portion, to contact an interior face of at least one of the pair of side walls, and slide into the front opening such that at least a portion of the finger shield is in contact with the interior face, and the finger shield includes a first portion having a first width measured in a direction perpendicular to a longitudinal axis of the sheath that fits into the front opening, a second portion having a second width measured in said direction greater than the first width, and the second width not fitting into the front opening when the finger shield is in the closed position.

4. The sheath according to claim 3, wherein friction force caused by said contact between the finger shield and the interior face secures the finger shield in the closed position.

5. The sheath according to claim 4, wherein the friction force is between the first portion and the interior face.

6. The sheath according to claim 5, wherein the first portion is immediately adjacent to the second portion, and an edge of the second portion contacts one of the sidewalls when the finger shield is in the closed position.

\* \* \* \* \*